US008597170B2

(12) United States Patent
Walters et al.

(10) Patent No.: US 8,597,170 B2
(45) Date of Patent: Dec. 3, 2013

(54) CATHETER PUMP

(75) Inventors: Daniel A. Walters, Rockaway Township, NJ (US); William James Repka, Parsippany-Troy Hills, NJ (US); Kevin J. Powell, Glen Gardner, NJ (US); Richard L. Keenan, Livermore, CA (US); Justin M. Walsh, Spring Mills, PA (US); Robert L. Campbell, Port Matilda, PA (US); Mark W. McBride, Bellefonte, PA (US)

(73) Assignees: Thoratec Corporation, Pleasanton, CA (US); The Penn State Research Foundation, University Park, PA (US)

( * ) Notice: Subject to any disclaimer, the term of this patent is extended or adjusted under 35 U.S.C. 154(b) by 0 days.

(21) Appl. No.: 13/343,618

(22) Filed: Jan. 4, 2012

(65) Prior Publication Data

US 2012/0172656 A1 Jul. 5, 2012

Related U.S. Application Data

(60) Provisional application No. 61/430,129, filed on Jan. 5, 2011.

(51) Int. Cl.
*A61N 1/362* (2006.01)

(52) U.S. Cl.
USPC .......................................................... 600/16

(58) Field of Classification Search
USPC .......................................................... 600/16
See application file for complete search history.

(56) References Cited

U.S. PATENT DOCUMENTS

| 1,902,418 | A | 3/1933 | Pilgrim |
| 2,356,659 | A | 10/1942 | Aguiar |
| 2,649,052 | A | 8/1953 | Weyer |
| 2,664,050 | A | 12/1953 | Abresch |
| 2,684,035 | A | 7/1954 | Kemp |
| 2,789,511 | A | 4/1957 | Warren |
| 2,896,926 | A | 7/1959 | Chapman |
| 2,935,068 | A | 5/1960 | Donaldson |
| 3,080,824 | A | 3/1963 | Boyd et al. |

(Continued)

FOREIGN PATENT DOCUMENTS

| CA | 2367469 | 10/2000 |
| EP | 0 533 432 | 9/1992 |

(Continued)

OTHER PUBLICATIONS

Extended European Search Report dated Oct. 8, 2012, received in European Patent Application No. 07753903.9.

(Continued)

*Primary Examiner* — George Manuel
(74) *Attorney, Agent, or Firm* — Knobbe Martens Olson & Bear LLP

(57) ABSTRACT

A heart pump and a catheter assembly therefor are provided that include a flexible catheter body having a proximal end and a distal end, the catheter body having a plurality of lumens therethrough. The catheter body can be sufficiently flexible to extend from a peripheral access to a patient's heart. The catheter assembly can also include an impeller assembly having an impeller and a housing. The impeller assembly can be coupled with the flexible catheter body such that a tensile force applied to opposite ends of the catheter assembly enhances the security of the connection between the catheter body and the impeller assembly.

43 Claims, 21 Drawing Sheets

(56) References Cited

U.S. PATENT DOCUMENTS

| | | |
|---|---|---|
| 3,455,540 A | 7/1969 | Marcmann |
| 3,510,229 A | 5/1970 | Smith |
| 3,812,812 A | 5/1974 | Hurwitz |
| 3,860,968 A | 1/1975 | Shapiro |
| 3,904,901 A | 9/1975 | Renard et al. |
| 3,995,617 A | 12/1976 | Watkins et al. |
| 4,129,129 A | 12/1978 | Amrine |
| 4,135,253 A | 1/1979 | Reich et al. |
| 4,149,535 A | 4/1979 | Volder |
| 4,304,524 A | 12/1981 | Coxon et al. |
| 4,382,199 A | 5/1983 | Isaacson |
| 4,392,836 A | 7/1983 | Sugawara |
| 4,458,366 A | 7/1984 | MacGregor |
| 4,540,402 A | 9/1985 | Aigner |
| 4,560,375 A | 12/1985 | Schulte et al. |
| 4,589,822 A | 5/1986 | Clausen et al. |
| 4,625,712 A | 12/1986 | Wampler |
| 4,655,745 A | 4/1987 | Corbett |
| 4,686,982 A | 8/1987 | Nash |
| 4,704,121 A | 11/1987 | Moise |
| 4,728,319 A | 3/1988 | Masch |
| 4,753,221 A | 6/1988 | Kensey et al. |
| 4,769,006 A | 9/1988 | Papantonakos |
| 4,817,586 A | 4/1989 | Wampler |
| 4,846,152 A | 7/1989 | Wampler et al. |
| 4,895,557 A | 1/1990 | Moise et al. |
| 4,900,227 A | 2/1990 | Trouplin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,944,722 A | 7/1990 | Carriker et al. |
| 4,955,856 A | 9/1990 | Phillips |
| 4,957,504 A | 9/1990 | Chardack |
| 4,964,864 A | 10/1990 | Summers et al. |
| 4,969,865 A * | 11/1990 | Hwang et al. .................. 600/16 |
| 4,976,270 A | 12/1990 | Parl et al. |
| 4,985,014 A | 1/1991 | Orejola |
| 4,994,017 A | 2/1991 | Yozu |
| 4,995,857 A | 2/1991 | Arnold |
| 5,000,177 A | 3/1991 | Hoffman et al. |
| 5,021,048 A | 6/1991 | Buckholtz |
| 5,049,134 A | 9/1991 | Golding et al. |
| 5,089,016 A | 2/1992 | Millner et al. |
| 5,092,844 A | 3/1992 | Schwartz et al. |
| 5,098,256 A | 3/1992 | Smith |
| 5,106,368 A | 4/1992 | Uldall et al. |
| 5,112,200 A | 5/1992 | Isaacson et al. |
| 5,112,349 A | 5/1992 | Summers et al. |
| 5,129,883 A | 7/1992 | Black |
| 5,147,186 A | 9/1992 | Buckholtz |
| 5,163,910 A | 11/1992 | Schwartz et al. |
| 5,171,212 A | 12/1992 | Buck et al. |
| 5,190,528 A | 3/1993 | Fonger et al. |
| 5,201,679 A | 4/1993 | Velte et al. |
| 5,211,546 A | 5/1993 | Isaacson et al. |
| 5,290,227 A | 3/1994 | Pasque |
| 5,300,112 A | 4/1994 | Barr |
| 5,312,341 A | 5/1994 | Turi |
| 5,346,458 A | 9/1994 | Affeld |
| 5,360,317 A | 11/1994 | Clausen et al. |
| 5,376,114 A | 12/1994 | Jarvik |
| 5,393,207 A | 2/1995 | Maher et al. |
| 5,405,383 A | 4/1995 | Barr |
| 5,437,541 A | 8/1995 | Vainrub et al. |
| 5,449,342 A | 9/1995 | Hirose et al. |
| 5,458,459 A | 10/1995 | Hubbard et al. |
| 5,505,701 A | 4/1996 | Anaya Fernandez de Lomana |
| 5,527,159 A | 6/1996 | Bozeman, Jr. et al. |
| 5,533,957 A | 7/1996 | Aldea |
| 5,588,812 A | 12/1996 | Taylor et al. |
| 5,613,935 A | 3/1997 | Jarvik |
| 5,643,226 A | 7/1997 | Cosgrove et al. |
| 5,678,306 A | 10/1997 | Bozeman, Jr. et al. |
| 5,692,882 A | 12/1997 | Bozeman, Jr. et al. |
| 5,707,218 A | 1/1998 | Maher et al. |
| 5,722,930 A | 3/1998 | Larson et al. |
| 5,730,628 A | 3/1998 | Hawkins |
| 5,738,649 A | 4/1998 | Macoviak |
| 5,741,234 A | 4/1998 | Aboul-Hosn |
| 5,746,709 A | 5/1998 | Rom et al. |
| 5,749,855 A | 5/1998 | Reitan |
| 5,755,784 A | 5/1998 | Jarvik |
| 5,776,111 A | 7/1998 | Tesio |
| 5,779,721 A | 7/1998 | Nash |
| 5,807,311 A | 9/1998 | Palestrant |
| 5,814,011 A | 9/1998 | Corace |
| 5,824,070 A | 10/1998 | Jarvik |
| 5,851,174 A | 12/1998 | Jarvik et al. |
| 5,868,702 A | 2/1999 | Stevens |
| 5,868,703 A | 2/1999 | Bertolero |
| 5,888,242 A | 3/1999 | Antaki et al. |
| 5,911,685 A | 6/1999 | Siess et al. |
| 5,921,913 A | 7/1999 | Siess |
| 5,941,813 A | 8/1999 | Sievers et al. |
| 5,951,263 A | 9/1999 | Taylor et al. |
| 5,964,694 A | 10/1999 | Siess et al. |
| 6,007,478 A | 12/1999 | Siess et al. |
| 6,007,479 A | 12/1999 | Rottenberg et al. |
| 6,015,272 A | 1/2000 | Antaki et al. |
| 6,018,208 A | 1/2000 | Maher et al. |
| 6,056,719 A | 5/2000 | Mickley |
| 6,058,593 A | 5/2000 | Siess |
| 6,071,093 A | 6/2000 | Hart |
| 6,083,260 A | 7/2000 | Aboul-Hosn |
| 6,086,527 A | 7/2000 | Talpade |
| 6,086,570 A | 7/2000 | Aboul-Hosn et al. |
| 6,113,536 A | 9/2000 | Aboul-Hosn et al. |
| 6,123,659 A | 9/2000 | Le Blanc et al. |
| 6,123,725 A | 9/2000 | Aboul-Hosn |
| 6,132,363 A | 10/2000 | Freed et al. |
| 6,135,943 A | 10/2000 | Yu et al. |
| 6,136,025 A | 10/2000 | Barbut et al. |
| 6,139,487 A | 10/2000 | Siess |
| 6,152,704 A | 11/2000 | Aboul-Hosn et al. |
| 6,176,822 B1 | 1/2001 | Nix et al. |
| 6,176,848 B1 | 1/2001 | Rau et al. |
| 6,186,665 B1 | 2/2001 | Maher et al. |
| 6,190,304 B1 | 2/2001 | Downey et al. |
| 6,200,260 B1 | 3/2001 | Bolling |
| 6,210,133 B1 | 4/2001 | Aboul-Hosn et al. |
| 6,210,397 B1 | 4/2001 | Aboul-Hosn et al. |
| 6,227,797 B1 | 5/2001 | Watterson et al. |
| 6,228,063 B1 | 5/2001 | Aboul-Hosn |
| 6,234,960 B1 | 5/2001 | Aboul-Hosn et al. |
| 6,245,007 B1 | 6/2001 | Bedingham et al. |
| 6,247,892 B1 | 6/2001 | Kazatchkov et al. |
| 6,248,091 B1 | 6/2001 | Voelker Wolfram |
| 6,254,359 B1 | 7/2001 | Aber |
| 6,287,319 B1 | 9/2001 | Aboul-Hosn et al. |
| 6,295,877 B1 | 10/2001 | Aboul-Hosn et al. |
| 6,305,962 B1 | 10/2001 | Maher et al. |
| 6,387,037 B1 | 5/2002 | Bolling et al. |
| 6,395,026 B1 | 5/2002 | Aboul-Hosn et al. |
| 6,422,990 B1 | 7/2002 | Prem |
| 6,425,007 B1 | 7/2002 | Messinger |
| 6,428,464 B1 | 8/2002 | Bolling |
| 6,447,441 B1 | 9/2002 | Yu et al. |
| 6,503,224 B1 | 1/2003 | Forman et al. |
| 6,508,777 B1 | 1/2003 | Macoviak et al. |
| 6,508,787 B2 | 1/2003 | Erbel et al. |
| 6,517,315 B2 | 2/2003 | Belady |
| 6,517,528 B1 | 2/2003 | Pantages et al. |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | de Blanc et al. |
| 6,609,883 B2 | 8/2003 | Woodard et al. |
| 6,610,004 B2 | 8/2003 | Viole et al. |
| 6,613,008 B2 | 9/2003 | Aboul-Hosn et al. |
| 6,616,323 B2 | 9/2003 | McGill |
| 6,623,420 B2 | 9/2003 | Reich et al. |
| 6,641,558 B1 | 11/2003 | Aboul-Hosn et al. |
| 6,692,318 B2 | 2/2004 | McBride |

(56) References Cited

U.S. PATENT DOCUMENTS

| | | |
|---|---|---|
| 6,709,418 B1 | 3/2004 | Aboul-Hosn et al. |
| 6,716,189 B1 | 4/2004 | Jarvik et al. |
| 6,749,598 B1 | 6/2004 | Keren et al. |
| 6,776,578 B2 | 8/2004 | Belady |
| 6,783,328 B2 | 8/2004 | Lucke et al. |
| 6,790,171 B1 | 9/2004 | Grundeman et al. |
| 6,794,789 B2 | 9/2004 | Siess et al. |
| 6,814,713 B2 | 11/2004 | Aboul-Hosn et al. |
| 6,817,836 B2 | 11/2004 | Nose et al. |
| 6,860,713 B2 | 3/2005 | Hoover |
| 6,866,625 B1 | 3/2005 | Avre et al. |
| 6,866,805 B2 | 3/2005 | Hong et al. |
| 6,889,082 B2 | 5/2005 | Bolling et al. |
| 6,926,662 B1 | 8/2005 | Aboul-Hosn et al. |
| 6,935,344 B1 | 8/2005 | Aboul-Hosn et al. |
| 6,942,611 B2 | 9/2005 | Siess |
| 6,949,066 B2 | 9/2005 | Bearnson et al. |
| 6,966,748 B2 | 11/2005 | Woodard et al. |
| 6,972,956 B2 | 12/2005 | Franz et al. |
| 6,974,436 B1 | 12/2005 | Aboul-Hosn et al. |
| 6,981,942 B2 | 1/2006 | Khaw et al. |
| 6,984,392 B2 | 1/2006 | Bechert et al. |
| 7,010,954 B2 | 3/2006 | Siess et al. |
| 7,011,620 B1 | 3/2006 | Siess |
| 7,014,417 B2 | 3/2006 | Salomon |
| 7,022,100 B1 | 4/2006 | Aboul-Hosn et al. |
| 7,027,875 B2 | 4/2006 | Siess et al. |
| 7,037,069 B2 | 5/2006 | Arnold et al. |
| 7,070,555 B2 | 7/2006 | Siess |
| 7,122,019 B1 | 10/2006 | Kesten et al. |
| 7,125,376 B2 | 10/2006 | Viole et al. |
| 7,144,365 B2 | 12/2006 | Bolling et al. |
| 7,150,711 B2 | 12/2006 | Nusser et al. |
| 7,160,243 B2 | 1/2007 | Medvedev |
| 7,172,551 B2 | 2/2007 | Leasure |
| 7,175,588 B2 | 2/2007 | Morello |
| 7,241,257 B1 | 7/2007 | Ainsworth et al. |
| 7,264,606 B2 | 9/2007 | Jarvik et al. |
| 7,284,956 B2 | 10/2007 | Nose et al. |
| 7,329,236 B2 | 2/2008 | Kesten et al. |
| 7,331,921 B2 | 2/2008 | Viole et al. |
| 7,335,192 B2 | 2/2008 | Keren et al. |
| 7,341,570 B2 | 3/2008 | Keren et al. |
| 7,381,179 B2 | 6/2008 | Aboul-Hosn et al. |
| 7,393,181 B2 | 7/2008 | McBride |
| 7,491,163 B2 | 2/2009 | Viole et al. |
| 7,605,298 B2 | 10/2009 | Bechert et al. |
| 7,619,560 B2 | 11/2009 | Penna |
| 7,731,675 B2 | 6/2010 | Aboul-Hosn et al. |
| 7,766,892 B2 | 8/2010 | Keren et al. |
| 7,780,628 B1 | 8/2010 | Keren et al. |
| 7,785,246 B2 | 8/2010 | Aboul-Hosn et al. |
| 7,819,833 B2 | 10/2010 | Ainsworth et al. |
| 7,828,710 B2 | 11/2010 | Shifflette |
| 7,841,976 B2 | 11/2010 | Mc Bride et al. |
| 7,927,068 B2 | 4/2011 | McBride et al. |
| 7,942,804 B2 | 5/2011 | Khaw |
| 7,942,844 B2 | 5/2011 | Moberg et al. |
| 7,993,259 B2 | 8/2011 | Kang et al. |
| 7,998,054 B2 | 8/2011 | Bolling |
| 8,079,948 B2 | 12/2011 | Shifflette |
| 8,110,267 B2 | 2/2012 | Houston et al. |
| 8,177,703 B2 | 5/2012 | Smith et al. |
| 8,206,350 B2 | 6/2012 | Mann et al. |
| 8,277,470 B2 | 10/2012 | Demarais et al. |
| 8,364,278 B2 | 1/2013 | Pianca et al. |
| 8,376,707 B2 | 2/2013 | McBride et al. |
| 2002/0111663 A1 | 8/2002 | Dahl et al. |
| 2002/0151761 A1 | 10/2002 | Beizai et al. |
| 2003/0205233 A1 | 11/2003 | Aboul-Hosn et al. |
| 2003/0208097 A1 | 11/2003 | Aboul-Hosn et al. |
| 2003/0231959 A1 | 12/2003 | Snider |
| 2005/0049696 A1 | 3/2005 | Siess et al. |
| 2005/0085683 A1 | 4/2005 | Bolling et al. |
| 2005/0090883 A1 | 4/2005 | Westlund et al. |
| 2005/0135942 A1 | 6/2005 | Wood et al. |
| 2005/0165269 A9 | 7/2005 | Aboul-Hosn et al. |
| 2006/0018943 A1 | 1/2006 | Bechert et al. |
| 2006/0058869 A1 | 3/2006 | Olson et al. |
| 2006/0063965 A1 | 3/2006 | Aboul-Hosn et al. |
| 2006/0155158 A1 | 7/2006 | Aboul-Hosn |
| 2006/0264695 A1 | 11/2006 | Viole et al. |
| 2006/0270894 A1 | 11/2006 | Viole et al. |
| 2007/0100314 A1 | 5/2007 | Keren et al. |
| 2007/0233270 A1 | 10/2007 | Weber et al. |
| 2008/0004690 A1 | 1/2008 | Robaina |
| 2008/0031953 A1 | 2/2008 | Takakusagi et al. |
| 2008/0103442 A1 | 5/2008 | Kesten et al. |
| 2008/0103591 A1 | 5/2008 | Siess |
| 2008/0132748 A1 | 6/2008 | Shifflete |
| 2008/0167679 A1 | 7/2008 | Papp |
| 2008/0275290 A1 | 11/2008 | Viole et al. |
| 2009/0023975 A1 | 1/2009 | Marseille et al. |
| 2009/0062597 A1 | 3/2009 | Shifflette |
| 2009/0093764 A1 | 4/2009 | Pfeffer et al. |
| 2009/0093765 A1 | 4/2009 | Glenn |
| 2009/0093796 A1 | 4/2009 | Pfeffer et al. |
| 2009/0163864 A1 | 6/2009 | Breznock et al. |
| 2009/0171137 A1 | 7/2009 | Farnan et al. |
| 2009/0182188 A1 | 7/2009 | Marseille et al. |
| 2010/0087773 A1 | 4/2010 | Ferrari |
| 2010/0127871 A1 | 5/2010 | Pontin |
| 2010/0197994 A1 | 8/2010 | Mehmanesh |
| 2010/0210895 A1 | 8/2010 | Aboul-Hosn et al. |
| 2010/0286210 A1 | 11/2010 | Murata et al. |
| 2011/0004046 A1 | 1/2011 | Campbell et al. |
| 2011/0021865 A1 | 1/2011 | Aboul-Hosn et al. |
| 2011/0034874 A1 | 2/2011 | Reitan |
| 2011/0071338 A1 | 3/2011 | McBride et al. |
| 2011/0076439 A1 | 3/2011 | Zeilon |
| 2011/0236210 A1 | 9/2011 | McBride et al. |
| 2011/0257462 A1 | 10/2011 | Rodefeld |
| 2011/0270182 A1 | 11/2011 | Breznock et al. |
| 2012/0004495 A1 | 1/2012 | Bolling |
| 2012/0172655 A1 | 7/2012 | Campbell et al. |
| 2012/0178985 A1 | 7/2012 | Walters et al. |
| 2012/0178986 A1 | 7/2012 | Campbell et al. |

FOREIGN PATENT DOCUMENTS

| | | |
|---|---|---|
| EP | 1207934 | 5/2002 |
| EP | 2151257 A1 | 2/2010 |
| EP | 2 263 732 A2 | 12/2010 |
| FR | 2267800 | 4/1974 |
| JP | S48-23295 | 3/1973 |
| JP | H06-114101 | 4/1994 |
| JP | H08-196624 | 8/1996 |
| JP | 10-099447 | 4/1998 |
| JP | 2002-505168 | 2/2002 |
| JP | 2011-000620 | 9/2005 |
| JP | 2011-157961 | 8/2011 |
| WO | WO 89/04644 | 6/1989 |
| WO | WO 89/05164 A1 | 6/1989 |
| WO | WO 94/06486 | 3/1994 |
| WO | WO 97/15228 | 5/1997 |
| WO | WO 99/37352 | 7/1999 |
| WO | WO 00/12148 | 3/2000 |
| WO | WO 00/18448 | 4/2000 |
| WO | WO 00/19097 | 4/2000 |
| WO | WO 00/043053 | 7/2000 |
| WO | WO 00/45874 | 8/2000 |
| WO | WO 00/61207 | 10/2000 |
| WO | WO 00/69489 | 11/2000 |
| WO | WO 01/24867 | 4/2001 |
| WO | WO 02/070039 | 9/2002 |
| WO | WO 03/068303 | 8/2003 |
| WO | WO 03/103745 | 12/2003 |
| WO | WO 2005/089674 | 9/2005 |
| WO | WO 05/123158 | 12/2005 |
| WO | WO 2007/112033 | 10/2007 |
| WO | WO 08-034068 | 3/2008 |
| WO | WO 2009/073037 | 6/2009 |
| WO | WO 2010/127871 | 11/2010 |
| WO | WO 2010/149393 | 12/2010 |

(56) References Cited

FOREIGN PATENT DOCUMENTS

| WO | WO 2011/003043 | 1/2011 |
|---|---|---|
| WO | WO 2011/035926 | 3/2011 |
| WO | WO 2011/035929 | 3/2011 |
| WO | WO 2011/076439 | 6/2011 |
| WO | WO 2011/089022 | 7/2011 |
| WO | WO 2012/007140 | 1/2012 |
| WO | WO 2012/007141 | 1/2012 |

OTHER PUBLICATIONS

ABIOMED—Recovering hearts. Saving lives., Impella 2.5 System, Instructions for Use, Jul. 2007, 86 sheets.

Cardiovascular Diseases (CVDs) Fact Sheet No. 317. World Health Organization. [Online] Sep. 2011. http://www.who.int/mediacentre/factsheets/fs317/en/index.html, accessed on Aug. 29, 2012.

European Search Report received from the European Patent Office in EP Application No. EP 05799883.3 dated May 10, 2011, 4 pages.

Ide, Hirofumi et al., Evaluation of the Pulsatility of a New Pulsatile Left Ventricular Assist Device—the Integrated Cardioassist Catheter—in Dogs, J. of Thoracic and Cardiovascular Surgery 107 (2): 569-75; Feb. 1994.

Ide, Hirofumi et al., Hemodynamic Evaluation of a New Left Ventricular Assist Device, Artificial Organs 16 (3): 286-90; 1992.

International Preliminary Examination Report from the European Patent Office received in PCT Application No. PCT/US2003/04853, mailed Jul. 26, 2004, 5 pages.

International Preliminary Examination Report from the European Patent Office received in PCT Application No. PCT/US2003/04401, mailed May 18, 2004, 4 pages.

International Preliminary Report on Patentability and Written Opinion of the International Searching Authority received in PCT Application No. PCT/US2005/033416, mailed Mar. 20, 2007, 7 pages.

International Preliminary Report on Patentability of the International Searching Authority received in PCT Application No. PCT/US2007/007313, mailed Sep. 23, 2008, 6 pages.

International Search Report and Written Opinion received in PCT Application No. PCT/US2005/33416, mailed Dec. 11, 2006, 4 pages.

International Search Report and Written Opinion received in PCT Application No. PCT/US2007/07313, mailed Mar. 4, 2008, 8 pages.

International Search Report received in PCT Application No. PCT/US2003/04401, mailed Nov. 10, 2003, 9 pages.

International Search Report received in PCT Application No. PCT/US2003/04853, mailed Jul. 3, 2003, 3 pages.

International Search Report Written Opinion received in PCT Application No. PCT/US2010/040847 mailed on Dec. 14, 2010.

International Search Report and Written Opinion received in PCT Application No. PCT/US2012/020382, mailed Jul. 31, 2012.

International Search Report and Written Opinion received in PCT Application No. PCT/US2012/020369 mailed Jul. 30, 2012.

International Search Report and Written Opinion received in PCT Application No. PCT/US2012/020553 mailed Aug. 17, 2012.

International Search Report and Written Opinion received in PCT Application No. PCT/US2012/020383 mailed Aug. 17, 2012.

Mihaylov, D. et al., Evaluation of the Optimal Driving Mode During Left Ventricular Assist with Pulsatile Catheter Pump in Calves, Artificial Organs 23(12): 1117-22; 1999.

Mihaylov, Dimiter et al., Development of a New Introduction Technique for the Pulsatile Catheter Pump, Artificial Organs 21(5): 425-27; 1997.

Morsink, PLJ et al., Numerical Modelling of Blood Flow Behaviour in the Valved Catheter of the PUCA Pump, a LVAD, The International Journal of Artificial Organs 20(5): 277-284; 1997.

Nishimura et al. The enabler cannula pump: a novel circulatory support system. The International Journal of Artificial Organs, vol. 22, No. 5, 1999, pp. 317-323.

Rakhorst, Gerhard et al., In Vitro Evaluation of the Influence of Pulsatile Intraventricular Pumping on Ventricular Pressure Patterns, Artificial Organs 18(7): 494-99; 1994.

Reitan, Oyvind, et al., Hydrodynamic Properties of a New Percutaneous Intra-aortic Axial Flow Pump. Reitan et al. ASAIO Journal 2000. pp. 323-328.

Schmitz-Rode, Thomas et al., "An Expandable Percutaneous Catheter Pump for Left Ventricular Support", Journal of the American College of Cardiology, vol. 45, No. 11, 2005, pp. 1856-1861.

Sharony et al. Cardiopulmonary Support and Physiology—The Intra-Aortic Cannula Pump: A Novel Assist Device for the Acutely Failing Heart. The Journal of Thoracic and Cardiovascular Surgery, Nov. 1992, vol. 118, No. 5, pp. 924-929.

Sharony, R. et al. Right heart support during off-pump coronary artery surgery—a multi-center study. Heart Surg Forum. 2002;5(1):13-6.

"Statistical Analysis and Clinical Experience with the Recover® Pump Systems", Impella CardioSystems GmbH, 2 sheets.

Supplementary European Search Report received from the European Patent Office in EP Application No. EP 05799883 dated Mar. 19, 2010, 3 pages.

Takagaki et al. A Novel Miniature Ventricular Assist Device for Hemodynamic Support. ASAIO Journal 2001, pp. 412-416.

Verkerke, Gijsbertus et al., Numerical Simulation of the Pulsating Catheter Pump: A Left Ventricular Assist Device, Artificial Organs 23(10): 924-31; 1999.

Verkerke, Bart et al., The PUCA Pump: A Left Ventricular Assist Device, Artificial Organs 17(5): 365-68; 1993. cited by other.

Verkerke, CJ et al., Numerical Simulation of the PUCA Pump, A Left Ventricular Assist Device, Abstracts of the XIXth ESAO Congress, The International Journal of Artificial Organs 15(9): 543; 1992.

Wampler, Richard. K., et al., The Sternotomy Hemopump, A Second Generation Intraarterial Ventricular Assist Device; Johnson and Johnson Interventional Systems, pp. M218-M220, 223, 1993.

Written Opinion received in PCT Application No. PCT/US2003/04853, dated Feb. 25, 2004, 5 pages.

ABIOMED—Impella 5.0 with the Impella Console, Circulatory Support System, Instructions for Use & Clinical Reference Manual, Jun. 2010, in 122 pages.

Barras et al., "Nitinol—Its Use in vascular Surgery and Other Applications," Eur J. Vasc Endovasc Surg, 2000, pp. 564-569, vol. 19.

Biscarini et al., "Enhanced nitinol properties for biomedical applications," Recent Patents on Biomedical Engineering, 2008, pp. 180-196, vol. 1(3).

Duerig et al., "An Overview of nitinol Medical Applications," Mat Sci Eng, 1999, pp. 149-160.

Grech, "Percutaneous Coronary Intervention. I: History and Development," BMJ.com, May 17, 2003, pp. 1080-1082, vol. 326.

Hsu et al., "Review of Recent Patents on Foldable Ventricular Assist Devices," Recent Patents on Biomedical Engineering, 2012, pp. 208-222, vol. 5.

Krishnamani et al., "Emerging Ventricular Assist Devices for Long-Term Cardiac Suport," Nature's Review, Cardiology, Feb. 2010, pp. 71-76, vol. 7.

Morgan, "Medical Shape Memory Alloy Applications—The Market and its Products," Materials Science and Engineering A, 2004, pp. 16-23, vol. 378.

Nishimura et al., "The Enabler Cannula Pump: A Novel Circulatory Support System," The International Journal of Artificial Organs, 1999, pp. 317-323; vol. 22(5).

Petrini et al., "Biomedical Applications of Shape Memory Alloys," Journal of Metallurgy, 2011, pp. 1-15.

Raess et al., "Impella 2.5," J. of Cardiovasc. Trans. Res., 2009; pp. 168-172; vol. 2(2).

Reitan et al., "Hemodynamic Effects of a New Percutaneous Circulatory Support Device in a Left Ventricular Failure Model," ASAIO Journal, 2003; pp. 731-736; vol. 49.

Shabari et al., "Improved Hemodynamics With a Novel Miniaturized Intra-Aortic Axial Flow Pump in a Porcine Model of Acute Left Ventricular Dysfunction," ASAIO Journal, 2013, pp. 240-245; vol. 59.

(56) References Cited

OTHER PUBLICATIONS

Smith et al., "First-In-Man Study of the Reitan Catheter Pump for Circulatory Support in Patients Undergoing High-Risk Percutaneous Coronary Intervention," Catheterization and Cardiovascular Interventions; 2009; pp. 859-865; vol. 73(7).

Sokolowski et al., "Medical Applications of Shape Memory Polymers," Biomed. Mater., 2007, pp. S23-S27; vol. 2(1).

Stoeckel et al., "Self-Expanding Nitinol Stents—Material and Design Considerations," European Radiology, 2003, pp. 292-301, vol. 14.

Throckmorton et al., "Flexible Impeller Blades in an Axial Flow Pump for Intravascular Cavopulmonary Assistance of the Fontan Physiology," Cardiovascular Engineering and Technology, Dec. 2010, pp. 244-255, vol. 1(4).

* cited by examiner

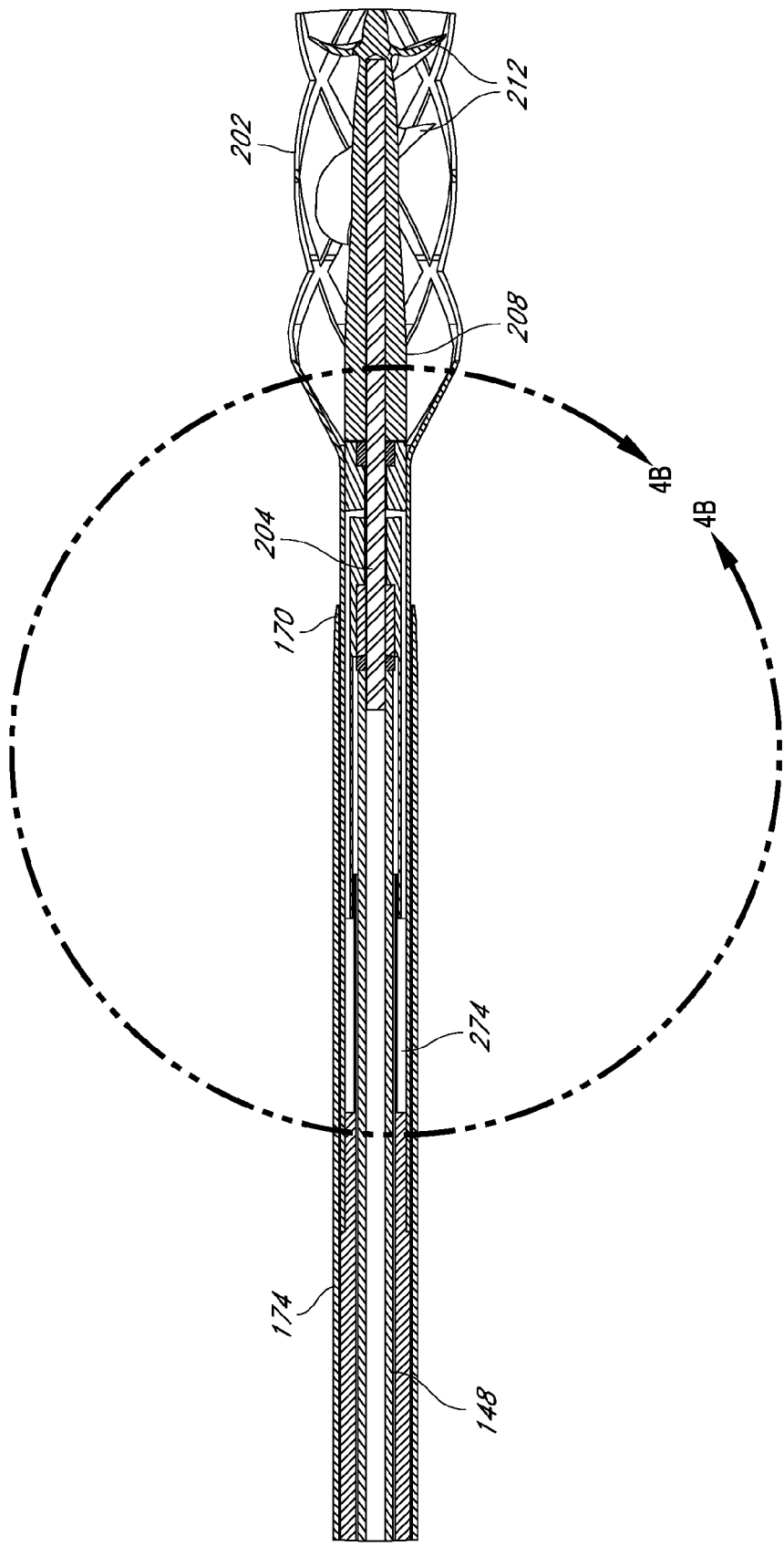

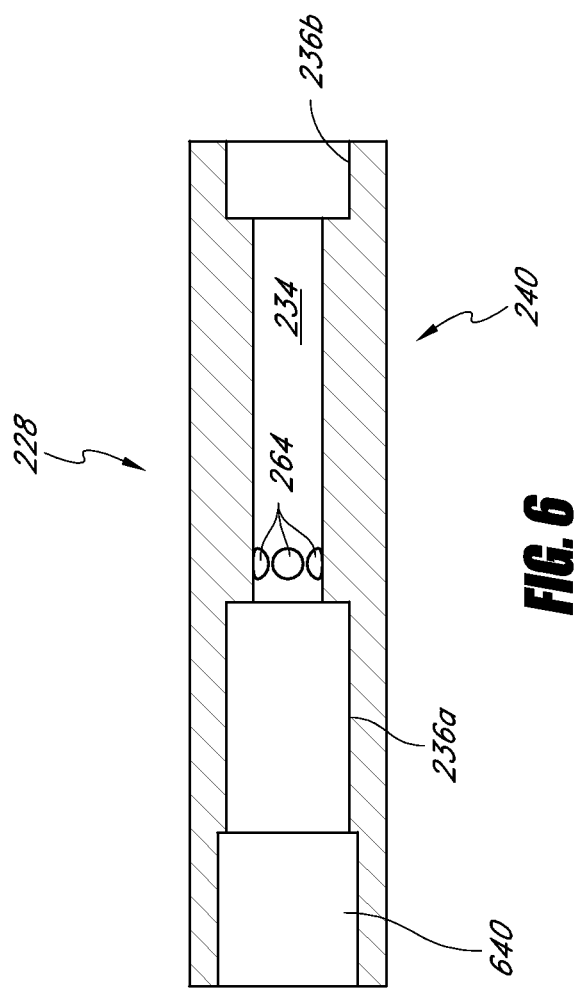

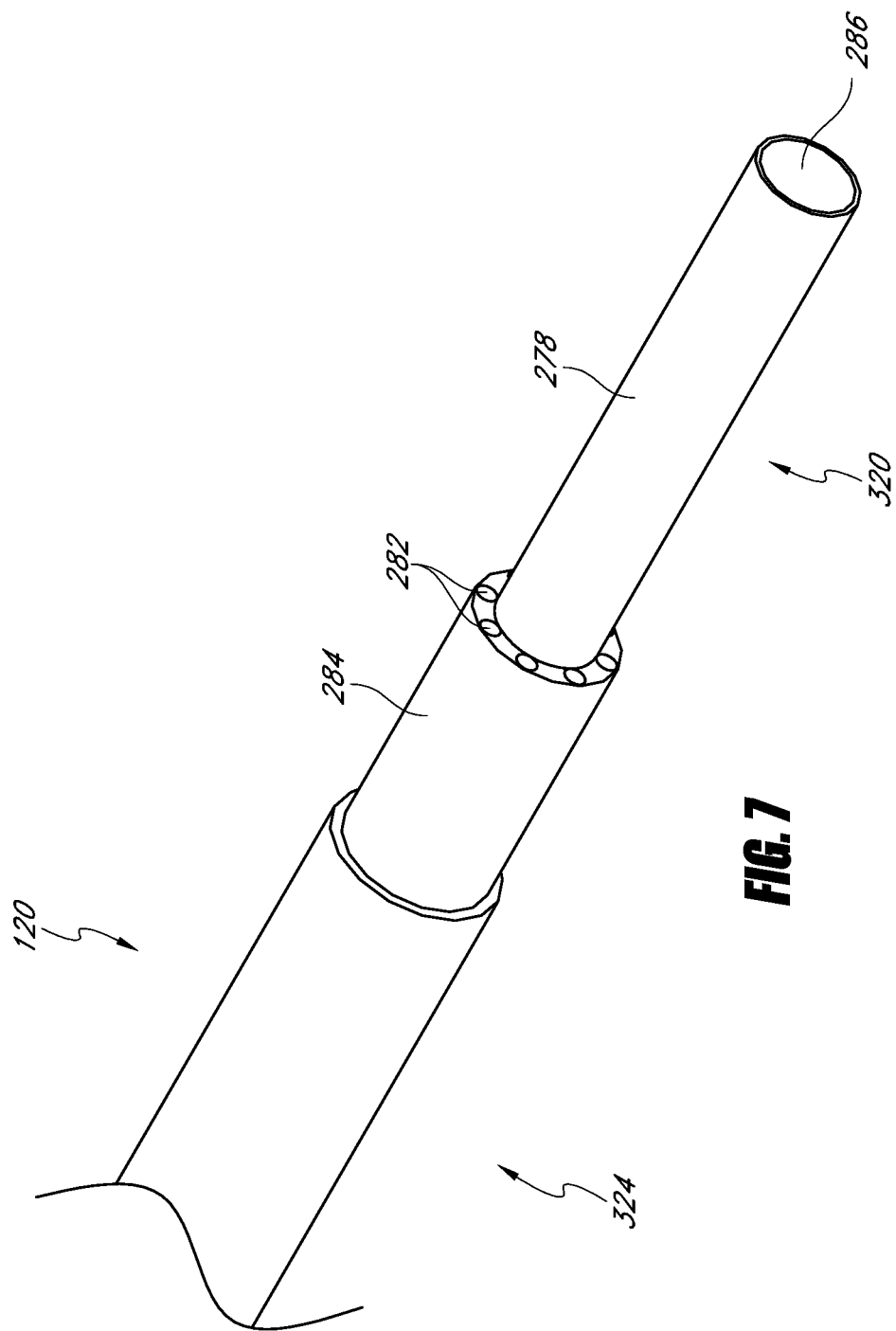

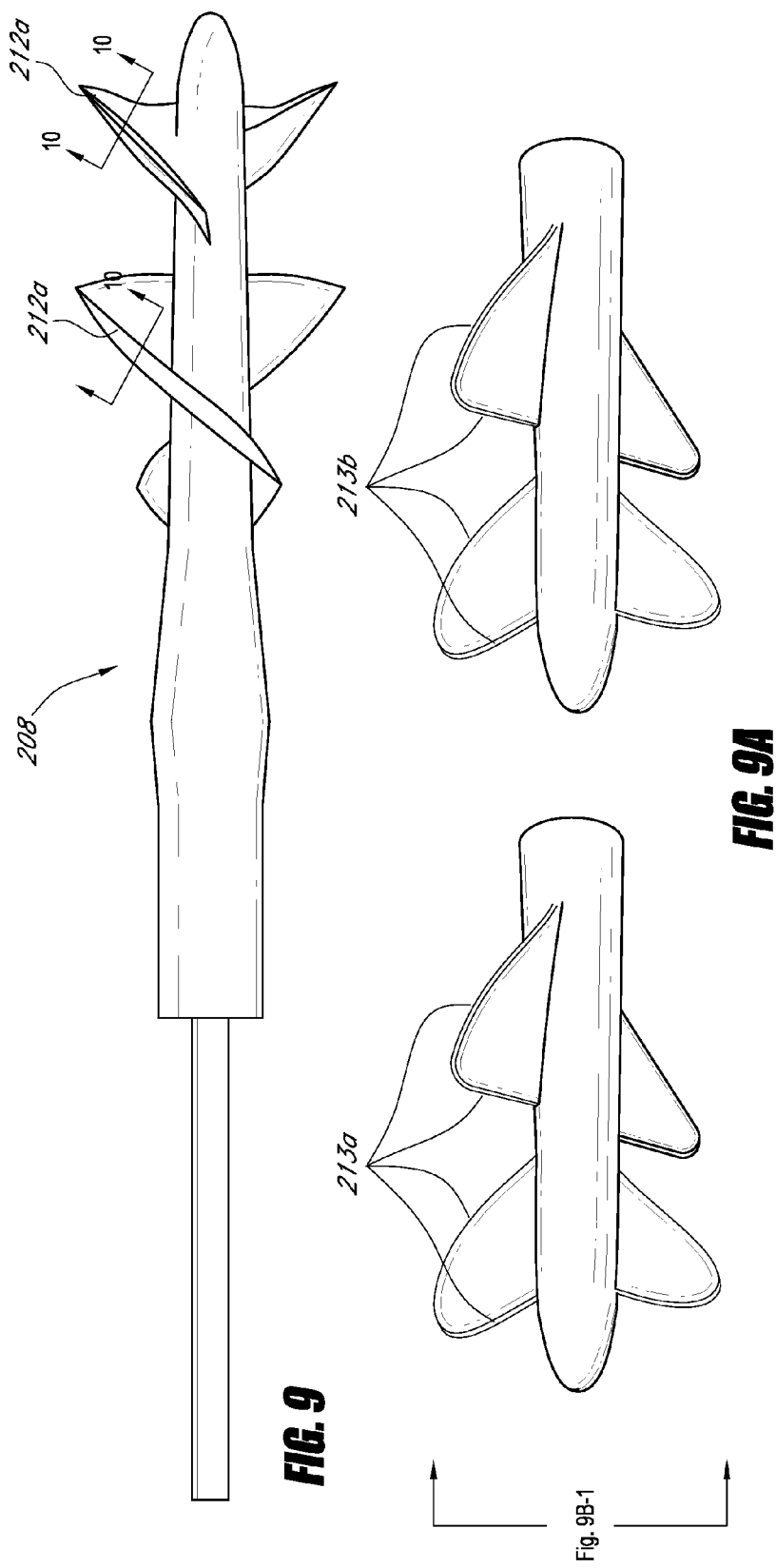

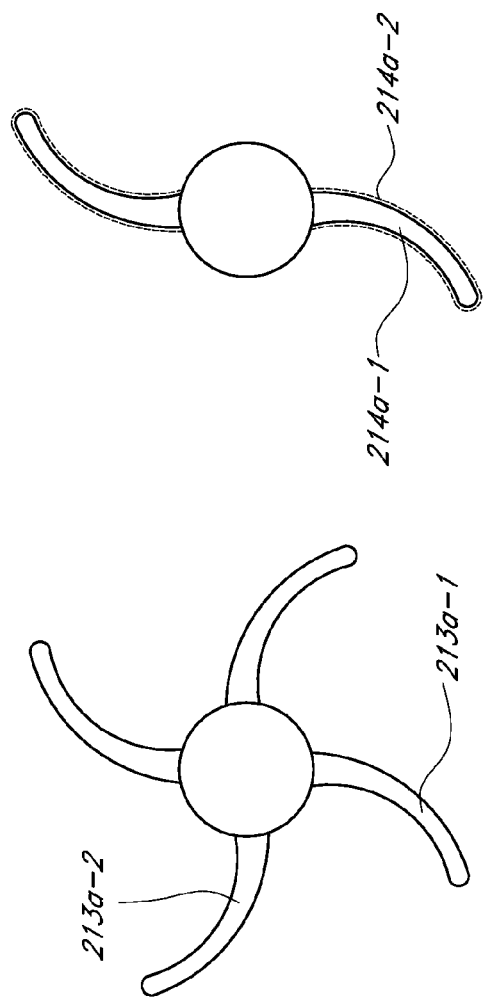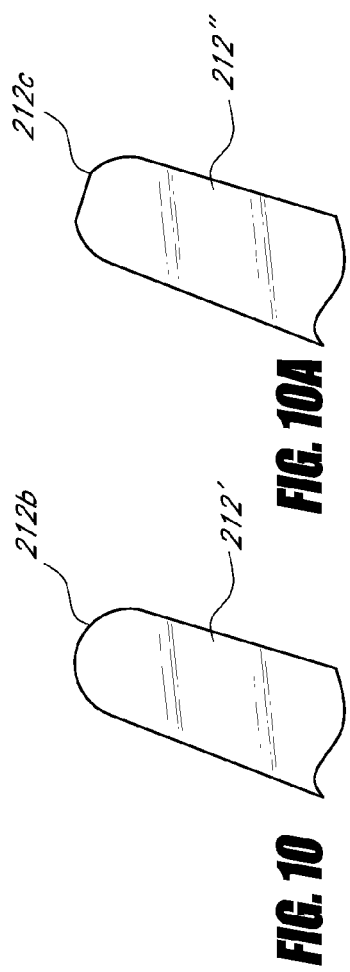

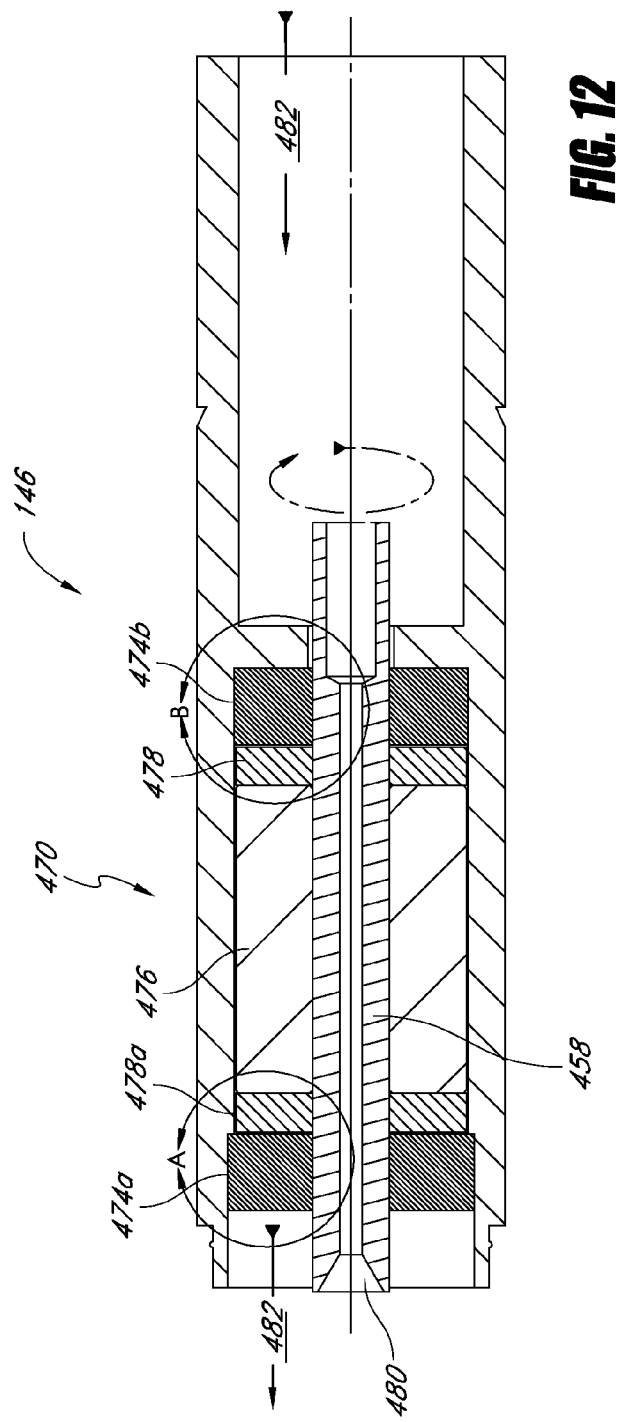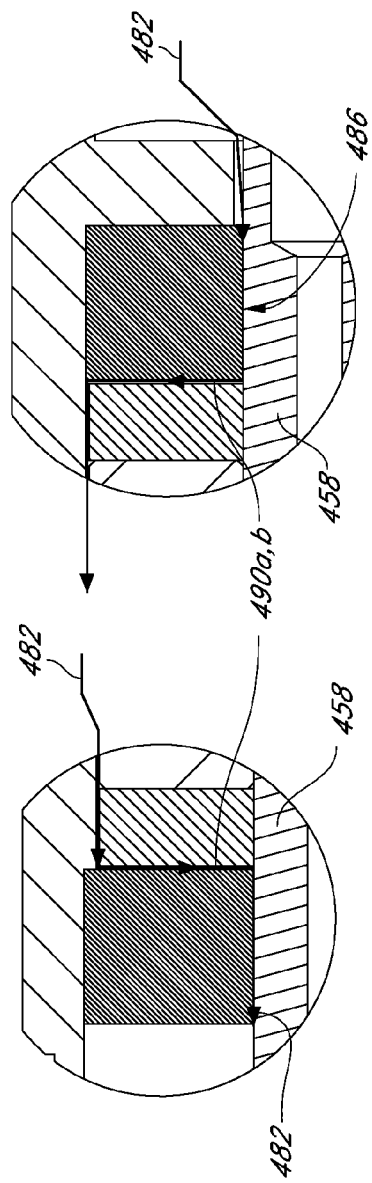

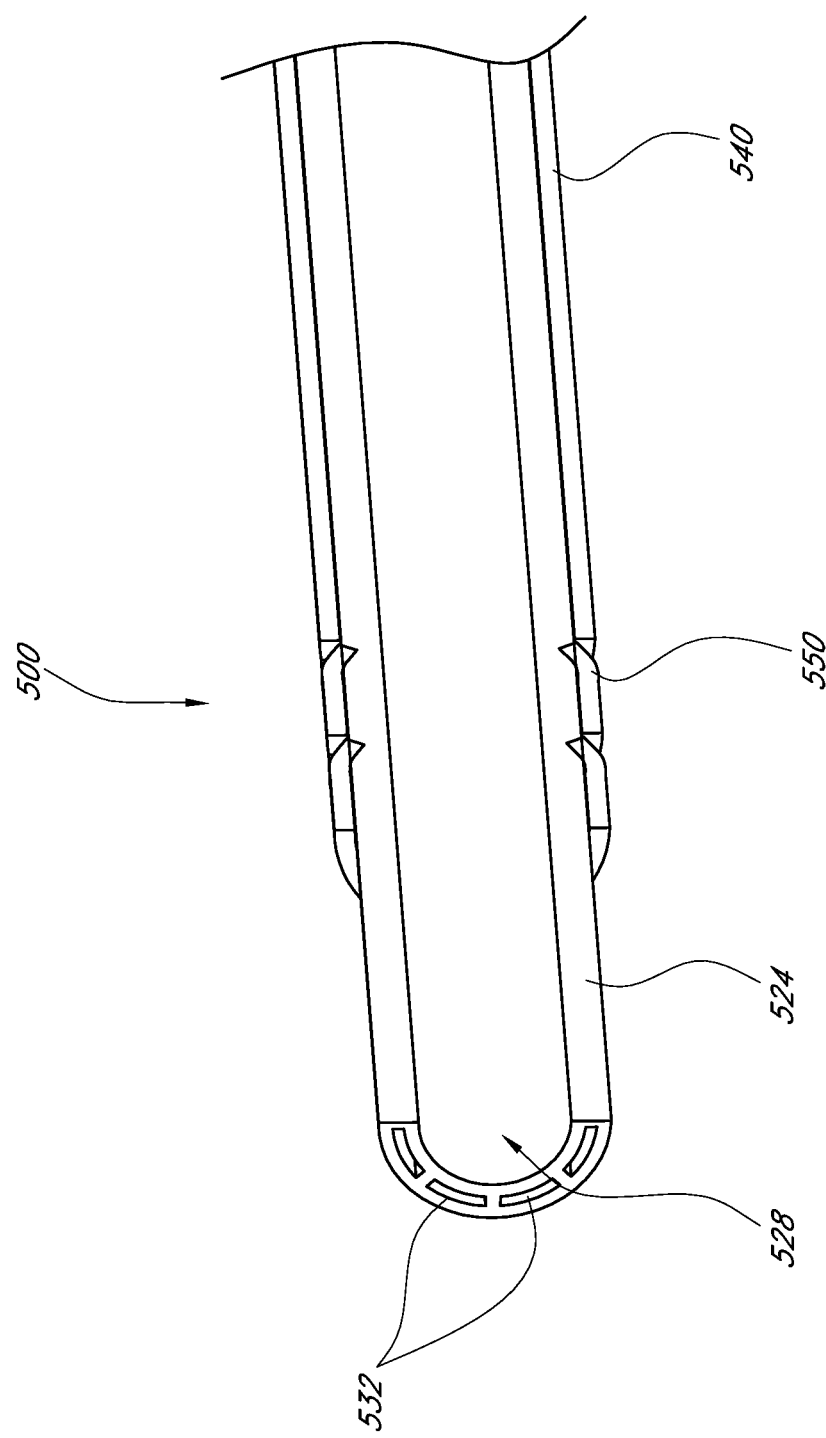

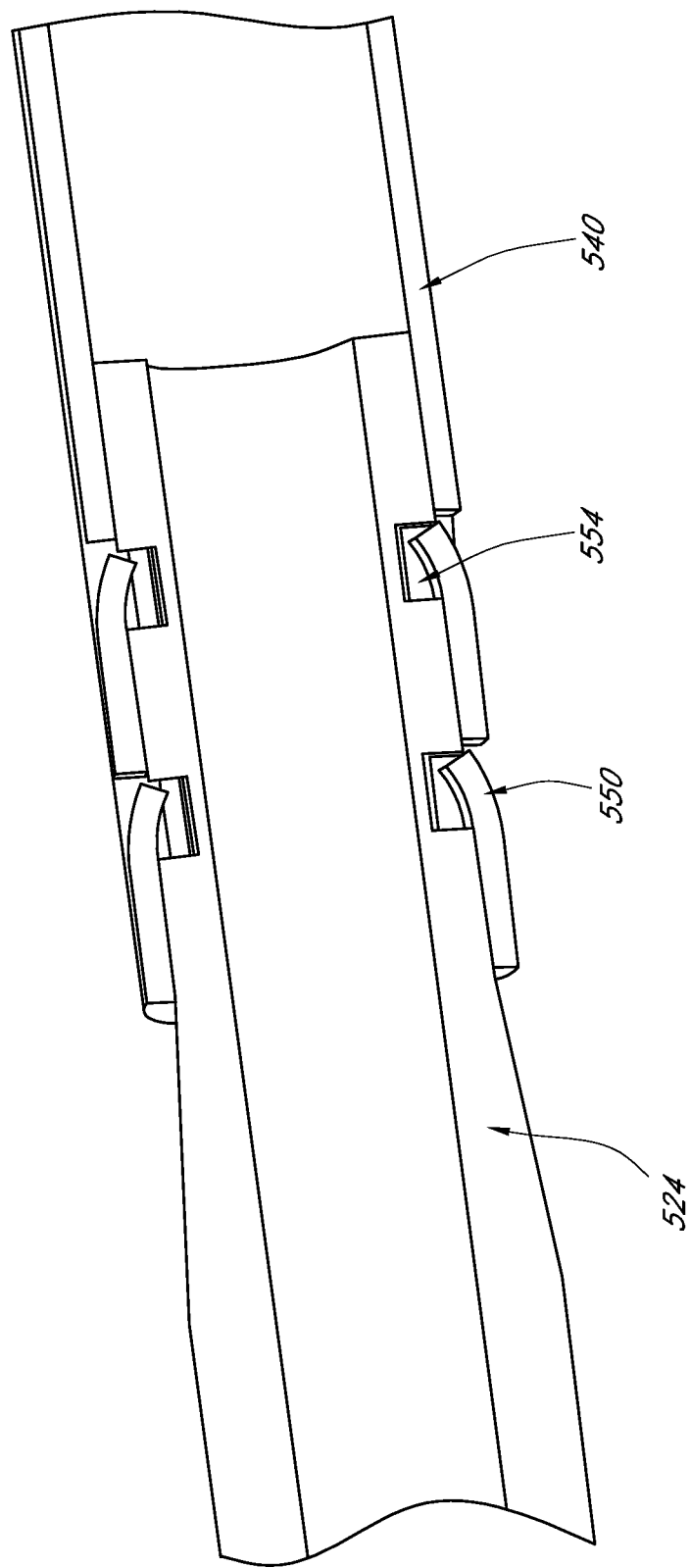

CATHETER PUMP

CROSS-REFERENCE TO RELATED APPLICATIONS

This application claims priority to U.S. Provisional Application Ser. No. 61/430,129 filed Jan. 5, 2011 entitled Percutaneous Heart Pump, which is hereby incorporated herein by reference for all purposes.

BACKGROUND OF THE INVENTION

1. Field of the Invention

This application is directed to heart pumps that can be applied percutaneously.

2. Description of the Related Art

Heart disease is a major health problem that claims many lives per year. After a heart attack, only a small number of patients can be treated with medicines or other non-invasive treatment. However, a significant number of patients can recover from a heart attack or cardiogenic shock if provided with mechanical circulatory support.

In a conventional approach, a blood pump having a fixed cross-section is surgically inserted a heart chamber, such as into the left ventricle of the heart and the aortic arch to assist the pumping function of the heart. Other known applications involve providing for pumping venous blood from the right ventricle to the pulmonary artery for support of the right side of the heart. The object of the surgically inserted pump is to reduce the load on the heart muscle for a period of time, which may be as long as a week, allowing the affected heart muscle to recover and heal. Surgical insertion, however, can cause additional serious stresses in heart failure patients.

Percutaneous insertion of a left ventricular assist device ("LVAD"), a right ventricular assist device ("RVAD") or in some cases a system for both sides of the heart (sometimes called biVAD) therefore is desired. Conventional fixed cross-section ventricular assist devices designed to provide near full heart flow rate are too large to be advanced percutaneously, e.g., through the femoral artery. There is an urgent need for a pumping device that can be inserted percutaneous and also provide full cardiac rate flows of the left, right, or both the left and right sides of the heart when called for.

SUMMARY OF THE INVENTION

In one embodiment, a heart pump is provided that includes a catheter assembly and an impeller assembly. The catheter assembly comprises a proximal end, a distal end, and an elongate body extending therebetween. The impeller is coupled with the elongate body. The impeller assembly comprises an impeller shaft and an impeller disposed on the impeller shaft. The heart pump also includes a bearing disposed between the proximal end of the impeller shaft and the distal end of the catheter assembly. The heart pump can optionally include a second bearing disposed between the first bearing and the proximal end of the catheter assembly. One or more bearings supporting the impeller shaft can be a hydrodynamic bearing. The heart pump also includes an infusant inflow port disposed distal of the bearing or between the first and second bearing (where provided) and configured to direct infusant toward the impeller shaft.

In another embodiment, a heart pump is provided that is configured to be applied percutaneously. The heart pump includes an impeller assembly and a catheter assembly comprising a proximal end, a distal end, and an elongate body extending therebetween. The impeller assembly includes an impeller shaft and an impeller disposed on the impeller shaft. The heart pump includes at least one bearing that supports the impeller assembly. The impeller bearing is configured to support the impeller assembly in a pressure-velocity range of about 20,000-50,000 psi-ft/min.

In other embodiments, the impeller bearing is configured to support the impeller assembly in a pressure-velocity range of about 35,000-50,000 psi-ft/min. However, even higher pressure-velocity ranges may be called for in certain embodiments, for example at least about 50,000 psi-ft/min in some embodiments, at least about 20,000 psi-ft/min in some embodiments and no less than 50 psi-ft/min in other embodiments.

In another embodiment, a heart pump is configured to be applied percutaneously and includes a catheter assembly, an impeller assembly and a drive shaft. The catheter assembly comprises a proximal end, a distal end, and an elongate body extending therebetween. The elongate body has a drive lumen extending therethrough. The impeller assembly comprises an impeller shaft and an impeller disposed on the impeller shaft. The drive shaft is disposed in the drive lumen and includes a plurality of layers.

In another embodiment, a heart pump is provided that is configured to be applied percutaneously. The heart pump includes a catheter assembly and an impeller assembly. The catheter assembly has a proximal end, a distal portion, and an elongate body extending therebetween. The distal portion has an expandable housing. The impeller assembly includes an impeller shaft and an impeller disposed on the impeller shaft. The impeller shaft is supported in the distal portion of the catheter assembly such that the impeller can be positioned in the expandable housing. At least the impeller comprises a layer disposed on a surface that is exposed to blood when the heart pump is inserted into the patient and operating. The layer is configured to enhance biocompatibility of the pump.

In another embodiment, a heart pump is provided that is configured to be applied percutaneously. The heart pump includes a catheter body and an impeller. The impeller includes a shaft and at least one blade coupled with the impeller. The impeller is rotated about a rotational axis and the blade extends radially outward from the rotational axis. A radially outermost portion has a rounded configuration. The rounded configuration eliminates sharp edges between at least one of a leading edge of the impeller blade, a radial end of the impeller blade, and a trailing edge of the impeller blade. In one embodiment, the rounded configuration provides a continuous curved profile from the leading edge to the trailing edge of the impeller blade.

In another embodiment, a catheter assembly for a heart pump is provided that can include a flexible catheter body having a proximal end and a distal end and defining a plurality of lumens therethrough. The catheter body can be sufficiently flexible to extend from a peripheral access to a patient's heart. The catheter assembly can also include an impeller assembly having an impeller and a housing. The impeller assembly can be coupled with the flexible catheter body such that a tensile force applied to opposite ends of the catheter assembly enhances the security of the connection between the catheter body and the impeller assembly.

BRIEF DESCRIPTION OF THE DRAWINGS

A more complete appreciation of the subject matter of the present inventions and the various advantages thereof can be realized by reference to the following detailed description, in which reference is made to the accompanying drawings in which:

FIG. 4A is a cross-sectional view of a distal portion of the catheter assembly, taken through the section plane 4A-4A shown in FIG. 2;

FIG. 6 is a cross-sectional view of a bearing housing of the bearing assembly of FIG. 5;

FIG. 7 is a perspective view of one embodiment of a catheter body that can be used to house a drive shaft and to convey an infusant to the bearing housing of FIG. 5;

FIG. 9 illustrates one embodiment of an impeller assembly;

FIGS. 9A, 9B-1, 9B-2, 10 and 10A illustrate details of further embodiments of impeller blade;

FIGS. 12, 12A, and 12B are cross-section views similar to that of FIG. 11, illustrating an infusant outflow path;

FIG. 13-15 illustrates various catheter assemblies that provide connection between a distal portion of a catheter body with a proximal portion of an impeller housing.

A more detailed description of various embodiments of components for heart pumps useful to treat patients experiencing cardiac stress, including acute heart failure, are set forth below.

DETAILED DESCRIPTION

Figure 1:
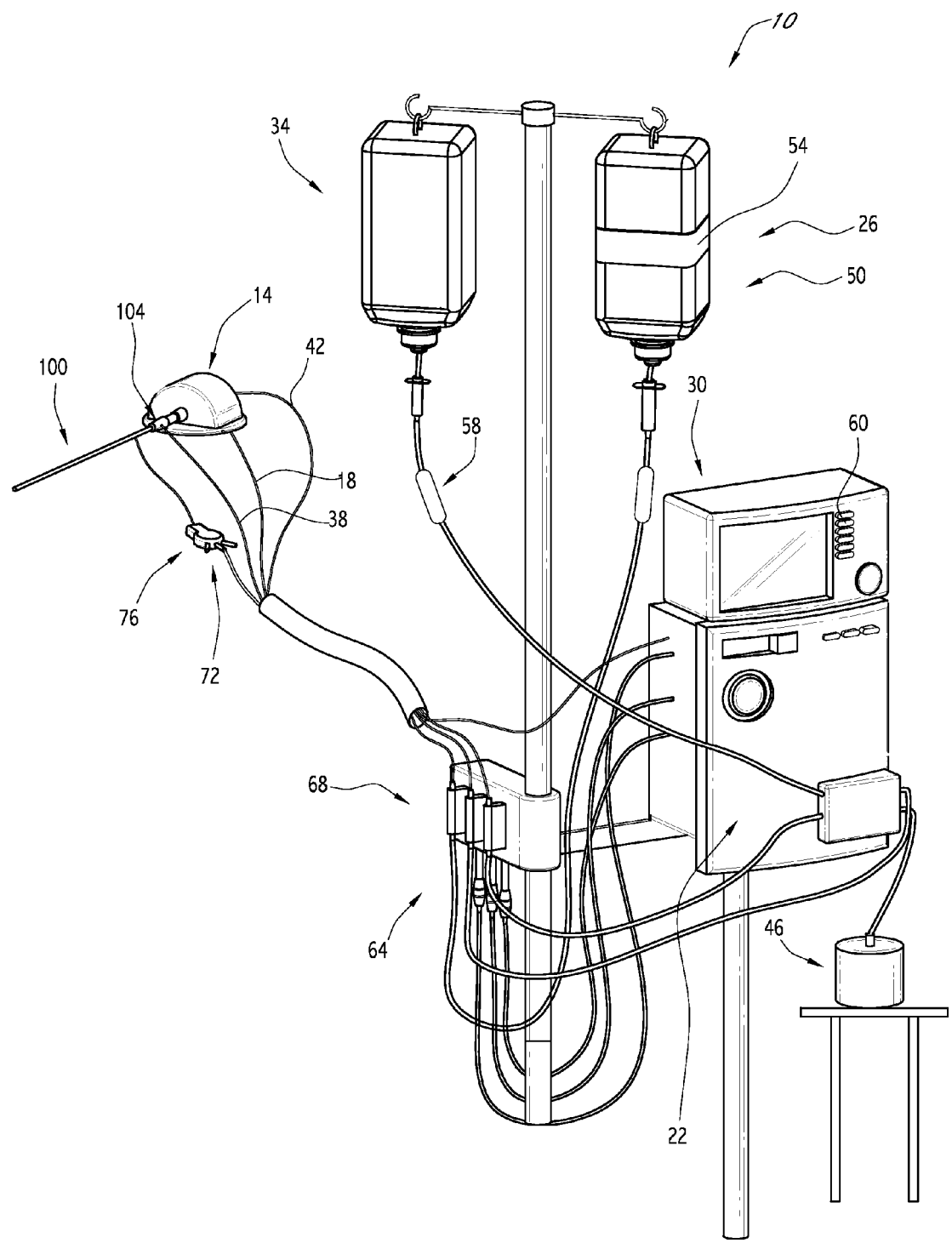
FIG. 1 illustrates one embodiment of a heart pump configured for percutaneous application and operation.

Major components of heart pumps that can be applied percutaneously to a patient are described below in Section I. Section II describes various structures that facilitate the rotatable support of a cantilevered impeller. Section III describes strategies for minimizing a patient's negative reaction to the presence of the systems within the cardiovascular system. Section IV illustrates structures for streamlined catheter assembly connections. Section V illustrates methods for use in connection with specific structures of heart pumps I. Overview of Heart Pumps FIG. 1 illustrates one embodiment of a heart pump 10 that includes a catheter assembly 100 having a proximal end 104 adapted to connect to a motor 14 and a distal end 108 (see FIG. 1A) adapted to be inserted percutaneously into a patient. The motor 14 is connected by a signal line 18 to a control module 22 that provides power and/or control signals to the motor 14. As discussed further below, the heart pump 10 may have an infusion system 26 and a patient monitoring system 30.

The infusion system 26 can provide a number of benefits to the heart pump 10 which are discussed below. In one embodiment, the infusion system 26 includes a source of infusant 34, a fluid conduit 38 extending from the infusant source 34 to the proximal end 104 of the catheter assembly 100 and a fluid conduit 42 extending from the proximal end of the catheter assembly 100 to a waste container 46. The flow of infusant to and from the catheter assembly 100 can be by any means, including a gravity system or one or more pumps. In the illustrated embodiment, the infusant source 34 includes an elevated container 50, which may be saline or another infusant as discussed below. Flow from the elevated container 50 can be regulated by a pressure cuff 54 to elevate the pressure of the fluid in the container 50 to increase flow or by a pinch valve 58 or by other means.

The patient monitoring system 30 can be used to monitor the operation of the patient and/or the pump 10. For example, the patient monitoring system 30 can include a user interface 60 coupled with a source of data 64. The data source 64 can include one or more patient conditions sensors, such as pressure sensors 68 that are in pressure communication with the patient and/or operating components within the patient. In one embodiment, the pressure sensors 68 fluidly communicate by a conduit 72 that extends between the sensors and a proximal portion of the catheter assembly 100. The conduit 72 can include a plurality of separable segments and can include a valve 76 to enable or disable the pressure communication to the sensors 68.

The heart pump 10 is adapted to provide an acute or other short-term treatment. A short-term treatment can be for less than a day or up to several days or weeks in some cases. With certain configurations the pump 10 can be used for a month or more.

The catheter assembly 100 extends between the proximal end 104 and the distal end 108. An impeller assembly 116 disposed at the distal end 108 is configured to pump blood to convey blood from one body cavity to another. In one arrangement, the impeller assembly 116 conveys blood proximally through or along a portion of the catheter assembly 100 to provide assistance to the left ventricle of the heart. In another embodiment, the impeller assembly 116 conveys blood distally through or along a portion of the catheter assembly 100 to provide assistance to the right ventricle of the heart. The heart pump 10 is useful as a heart assist device for treating patients with acute heart failure or other heart maladies. The heart pump 10 also can be used in connection with a surgical treatment to support the patient without providing full cardiovascular bypass. A patient could be supported on the device for longer term with proper controls and design.

The catheter assembly 100 is provided with a low profile configuration for percutaneous insertion. For example, the distal end 108 of the catheter assembly 100 can be configured to have about an 11 French (approximately 3.5 mm) size in a first configuration for insertion and an expanded configuration, such as up to about 21 French (approximately 7 mm), once positioned in the body. The larger size facilitates greater flow rates by the impeller assembly 116 as discussed below.

The catheter assembly 100 is configured to enable the distal end 108 to reach a heart chamber after being inserted initially into a peripheral vessel. For example, the catheter assembly 100 can have a suitable length to reach the left ventricle and sufficient pushability and torquability to traverse the intervening vasculature. The catheter assembly 100 may include a multilumen catheter body 120 that is arranged to facilitate delivery and operation of the impeller assembly 116. Further details concerning various embodiments of the catheter body 120 are discussed below in connection with FIGS. 7-7C.

A drive system is provided to drive an impeller within the impeller assembly 116. The drive system includes a motor 14 and a suitably configured drive controller (not shown). The motor 14 may be configured to be disposed outside the patient, e.g., adjacent to the proximal end 104 of the catheter assembly 100. In one advantageous embodiment, the drive system employs a magnetic drive arrangement. The motor 14 is arranged to generate magnetic fields that will be sensed by permanent magnets disposed within the proximal end 104 of the catheter assembly 100. This arrangement facilitates very efficient generation of torque used to drive the impeller assembly 116, as discussed below.

Some embodiments described herein could be incorporated into a system in which a motor is miniaturized sufficiently to be inserted into the patient in use, including into the vasculature. Such an embodiment could be operated by disposing control signal lines within the proximal portion of the catheter body 120. Also, it may be useful to provide the capability to measure blood pressure at the distal end 108 using a device disposed at the proximal end 104. For example, a pressure sensor at the distal end can communicate with a device outside the patient through a lumen of the catheter body 120. Various details of these optional features are described in U.S. Pat. No. 7,070,555, which is incorporate by reference herein in its entirety and for all purposes.

In another embodiment, a mechanical interface can be provided between the motor and the proximal end 104 of the catheter assembly 100. The mechanical interface can be between the motor 14 and a drive shaft positioned at the proximal end of the catheter assembly 100.

Figure 11:
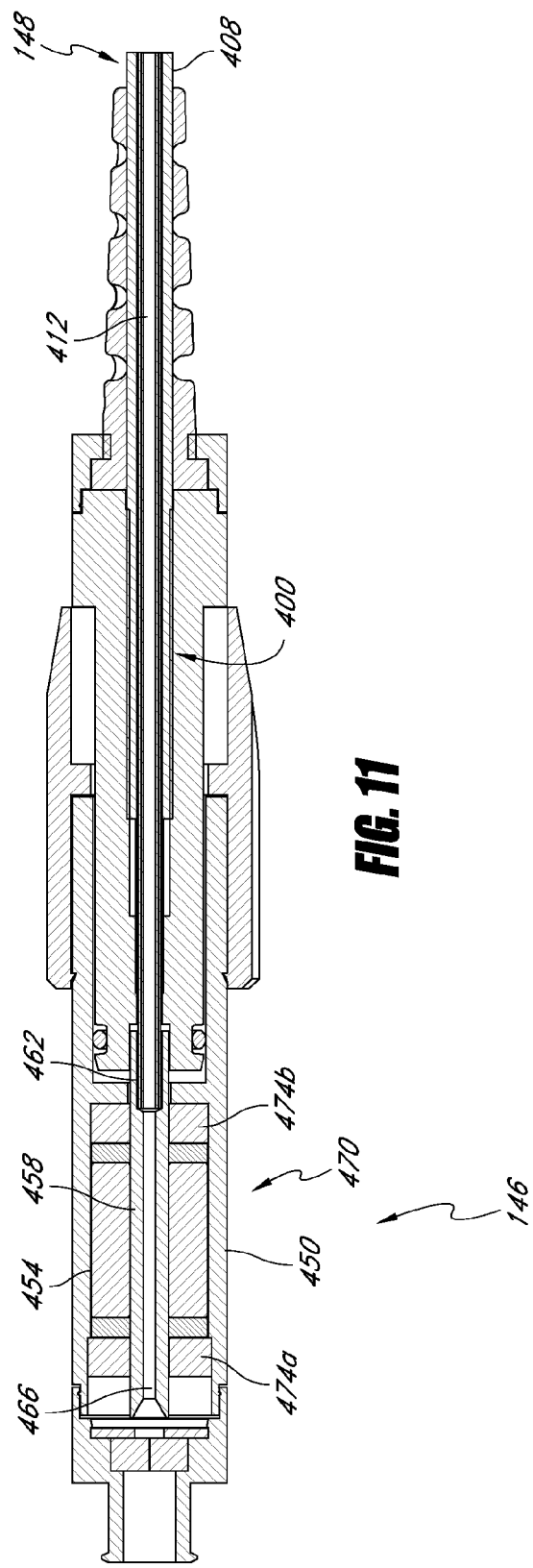
FIG. 11 is a cross-sectional view of a proximal portion of the catheter assembly, taken through the section plane 11-11 on FIG. 1A.

A torque coupling system is provided for transferring torque generated by the drive system to the impeller assembly 116. The torque coupling system is discussed further in Section II(C)—Torque Coupling System (as discussed below), but in general can include magnetic interface between the motor 14 and a drive assembly 146 disposed at the proximal end 104 of the catheter assembly 100. The drive assembly 146 is coupled with a proximal end of an elongate drive shaft 148 in one embodiment. The drive shaft 148 extends between the drive assembly 146 and the impeller assembly 116. A distal portion of the drive shaft 148 is coupled with the impeller assembly 116 as discussed below in connection with one embodiment illustrated in FIGS. 4A and 4B. FIG. 11 shows one manner of coupling the proximal end of the drive shaft 148 with the drive assembly 146.

Figure 1A:
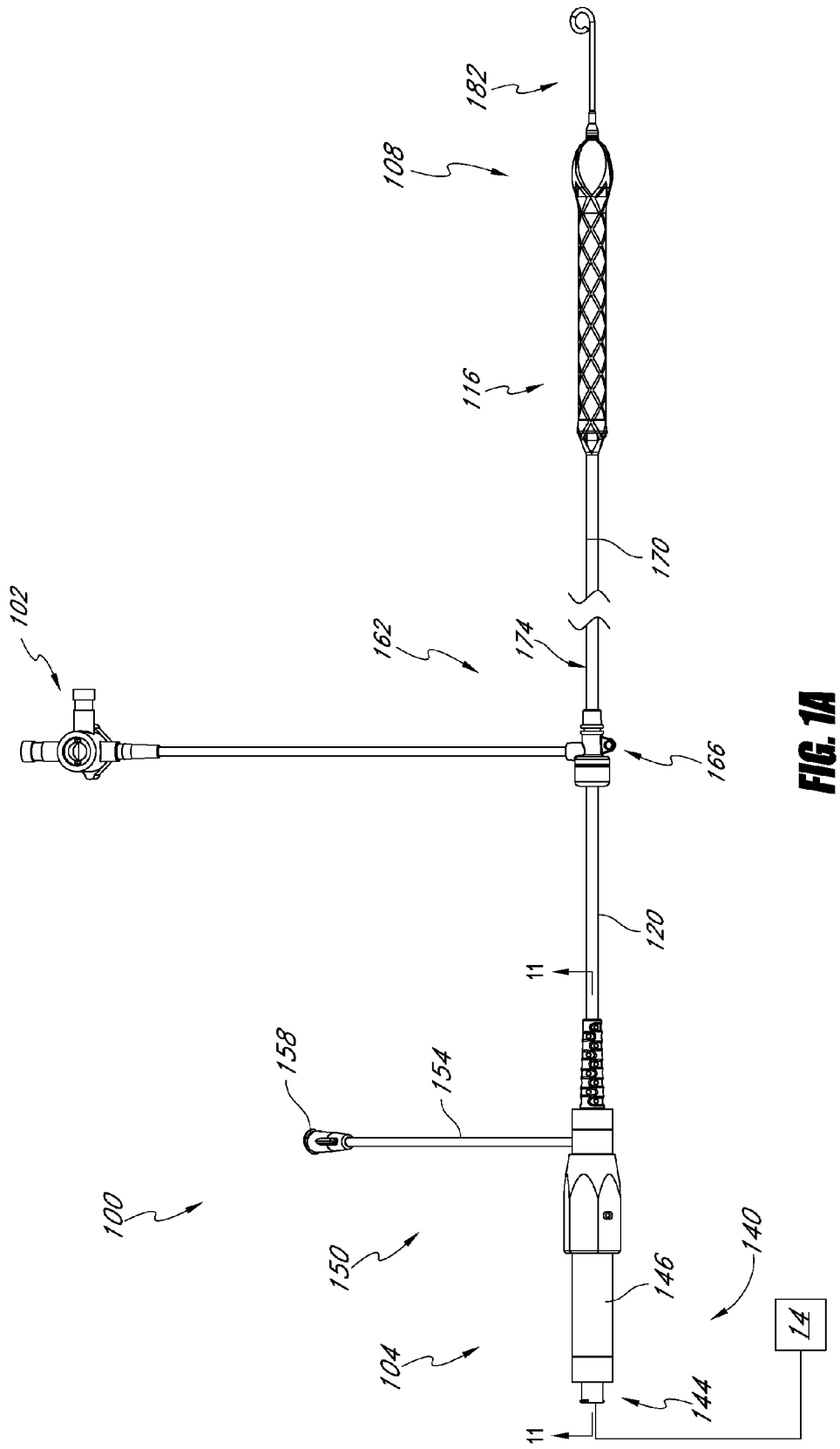
FIG. 1A is a plan view of one embodiment of a catheter assembly adapted to be used with the heart pump of FIG. 1.

As discussed above, the heart pump 10 may also include an infusion system 26. FIG. 1A shows that the infusion system 26 can include an infusion inflow assembly 150 provided adjacent to the proximal end 104 in one embodiment. The infusion assembly 150 can be one component of an infusion system that is configured to convey one or more fluids within the catheter assembly 100. The fluids can be conveyed distally within the catheter assembly 100, e.g., within the catheter body 120, to facilitate operation of the impeller assembly 116, some aspect of a treatment, or both. In one embodiment, the infusion system is configured to convey a lubricant, which, for example, can be saline, glucose, lactated Ringer's solution, acetated Ringer's solution, Hartmann's solution (a.k.a. compound sodium lactate), and D5W dextrose solution. In another embodiment, the infusion system is configured to convey a medication, or a substance that both acts as lubricant and medication. As sometimes used herein "infusant" is intended to be a broad term that includes any fluid or other matter that provides performance enhancement of a component of the heart pump 10 or therapeutic benefit, and can be wholly or partly extracted from the system during or after operation of the pump.

In one embodiment, the infusion inflow assembly 150 includes a catheter body 154 having a luer or other suitable connector 158 disposed at a proximal end thereof and an inflow port in fluid communication with one or more lumens within the catheter assembly 100. A lumen extending through the catheter body 154 is adapted to be fluidly coupled with a fluid source connected to the connector 158 to deliver the fluid into the catheter assembly 100 and through one or more flow paths as discussed below in connection with FIGS. 4A, 4B, and 7-7B.

FIGS. 1A and 12 show that the catheter assembly 100 may also include an outlet positioned at a location that is outside the patient when the heart pump 10 is in use to allow infusant to be removed from the pump and from the patient during or after the treatment. The outlet can be fluidly coupled with an infusant return flow path in the catheter body 120 through a fluid port 144 disposed at the proximal end 104.

The catheter assembly 100 can also include a sheath assembly 162 configured to constrain the impeller assembly 116 in a low profile configuration in a first state and to permit the impeller assembly 116 to expand to the enlarged configuration in a second state. The sheath assembly 162 has a proximal end 166, a distal end 170, and an elongate body 174 extending therebetween. In one embodiment, the elongate body 174 has a lumen extending between the proximal and distal ends 166, 170, the lumen being configured to be slidably disposed over the catheter body 120. The arrangement permits the sheath assembly 162 to be actuated between an advanced position and a retracted position. The retracted position is one example of a second state enabling the impeller assembly 116 to expand to an enlarged configuration. The advanced position is one example of a first state that enables the impeller assembly 116 to be collapsed to the low profile configuration. In some embodiments, a luer 102 or other suitable connector is in fluid communication with the proximal end 166 of the sheath assembly 162. The luer 102 can be configured to deliver fluids to the catheter assembly 100, such as priming fluid, infusant, or any other suitable fluid.

FIG. 1A illustrates a retracted position, in which the distal end 170 of the elongate body 174 is at a position proximal of the impeller assembly 116. In an advanced position, the distal end 170 of the elongate body 174 is positioned distal of at least a portion of the impeller assembly 116. The sheath assembly 162 can be configured such that distal advancement of the distal end 170 over the impeller assembly 116 actuates the impeller assembly 116 from an enlarged state to a more compact state (or low profile configuration), e.g., causing a change from the second state to the first state, as discussed above. Although shown in FIGS. 4A & 4B as a single layer, the elongate body 174 can include a multilayer construction.

Figure 4B:
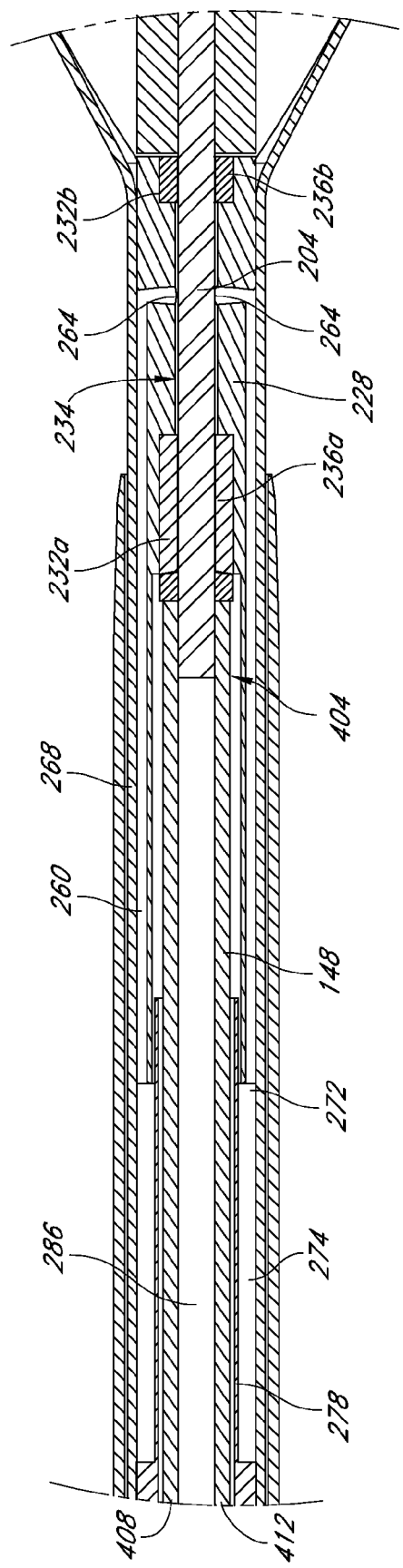
FIG. 4B is a detail view of the distal portion of the catheter assembly, taken at 4B-4B shown in FIG. 4A.

FIGS. 4A & 4B show the elongate body 174 as a single layer structure from the inner surface to the outer surface thereof. In another embodiment, the elongate body 174 has a multilayer construction. In one arrangement, the elongate body 174 has a first layer that is exposed to the catheter body 120 and a second layer exposed that corresponds to an outer surface of the catheter assembly 100. A third layer can be disposed between the first and second layers to reinforce the elongate body 174, particularly adjacent to the distal end thereof to facilitate collapse of the impeller assembly 116. In another construction, a reinforcing structure can be embedded in an otherwise continuous tubular structure forming the elongate body 174. For example, in some embodiments, the elongate body 174 can be reinforced with a metallic coil.

Figure 2:
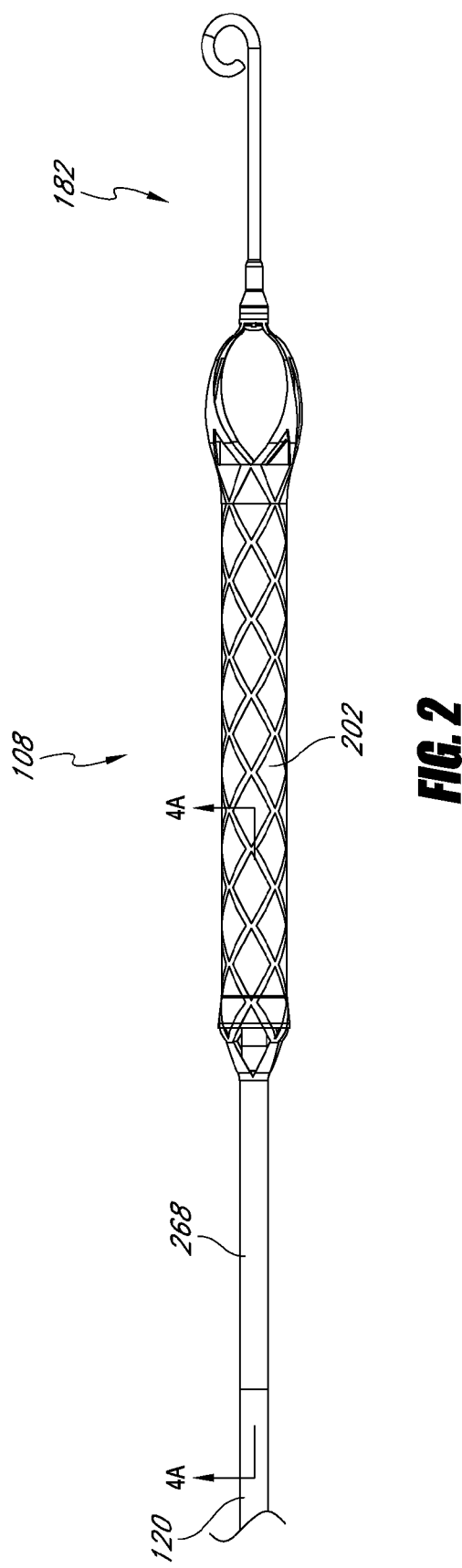
FIG. 2 is a detail view of a distal portion of the catheter assembly illustrated in FIG. 1A.

FIG. 2 show that an impeller housing 202 is disposed at the distal end 108. The impeller housing 202 can be considered part of the impeller assembly 116 in that it houses an impeller and provides clearance between the impeller and the anatomy to prevent any harmful interactions therebetween. The housing 202 and the impeller are also carefully integrated to maintain an appropriate flow regime, e.g., from distal to proximal or from proximal to distal within the housing.

FIGS. 1A and 2 also show that the distal end 108 of the catheter assembly 100 includes an atraumatic tip 182 disposed distal of the impeller assembly 116 in one embodiment. FIG. 1A shows that the atraumatic tip 182 can have an arcuate configuration such that interactions with the vasculature are minimally traumatic. The tip 182 can also be configured as a positioning member. In particular, the tip 182 can be flexible and compliant, yet rigid enough to help in positioning the impeller assembly 116 relative to the anatomy. In one embodiment, the tip 182 is rigid enough that when it is urged against a heart structure such as the ventricle wall, a tactile feedback is provided to the clinician indicating that the impeller assembly 182 is properly positioned against the heart structure.

II. Impeller Rotation and Support

The impeller assembly 116 can take any suitable form, but in various embodiments, includes an impeller 200 adapted to move a fluid such as blood from an inlet to an outlet of the catheter assembly 100. In certain embodiments the impeller 200 can be cantilevered or otherwise supported for rotation primarily at one end.

Figure 3:
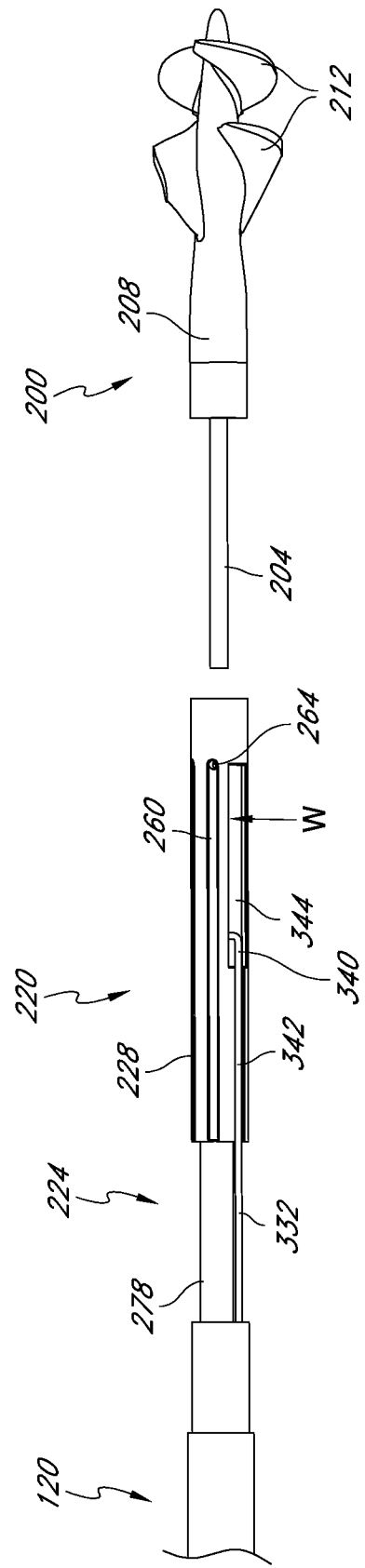
FIG. 3 is an exploded view of a portion of an impeller assembly of the catheter assembly of FIG. 1A.

FIG. 3 shows that the impeller 200 includes a shaft 204, a central body or hub 208, and one or more blades 212. Particular features of the impeller blades 212 are discussed further below in Section III(A).

The shaft 204 and hub 208 can be joined in any suitable fashion, such as by embedding a distal portion of the shaft within the hub 208. The blades 212 can be spaced out proximal to distal along the axis of the shaft. In some embodiments, the blades 212 are provided in blade rows. FIG. 9 shows that the distal end of the shaft 204 can extend at least to an axial position corresponding to one of the blade rows. In some embodiments, the shaft 204 can be solid. In other embodiments, the shaft 204 has a lumen extending axially through the hub so that a guidewire can be passed through the catheter assembly 100. Details of variations with a lumen are discussed further in U.S. application Ser. No. 12/829,359, filed Jul. 1, 2010, titled Blood Pump With Expandable Cannula, the contents of which are incorporated by reference herein in their entirety and for all purposes.

A. Infusant Delivery and Removal System

The operation and duty cycle of the impeller assembly 116 can be lengthened by providing a hydrodynamic bearing for supporting the shaft 204. A hydrodynamic bearing can be supported by a lubricant, such as isotonic saline, which can be delivered in a continuous flow. The lubricant can be delivered through the infusion system to an outside surface of the shaft 204. The infusant may be directed onto the shaft from a radially outward location. In some arrangements, the lubricant flow is controlled such that of a total lubricant volume introduced into the proximal end of the cannula, a first portion of the total volume of the lubricant flows proximally along the shaft 204. In some embodiments, a second portion of the total volume flows distally along the shaft, the first volume being different from the second volume. The second portion of the total volume can be substantially equal to the total volume introduced into the proximal end of the cannula less the first volume. Thus in one embodiment, infusant can be introduced that flows both in an axial and radial direction, for example, from proximal to distal, and radially outward. A small portion of the total infusant introduced can escape from the impeller assembly but most of the total infusant flows from distal back to a proximal direction.

Figure 16:
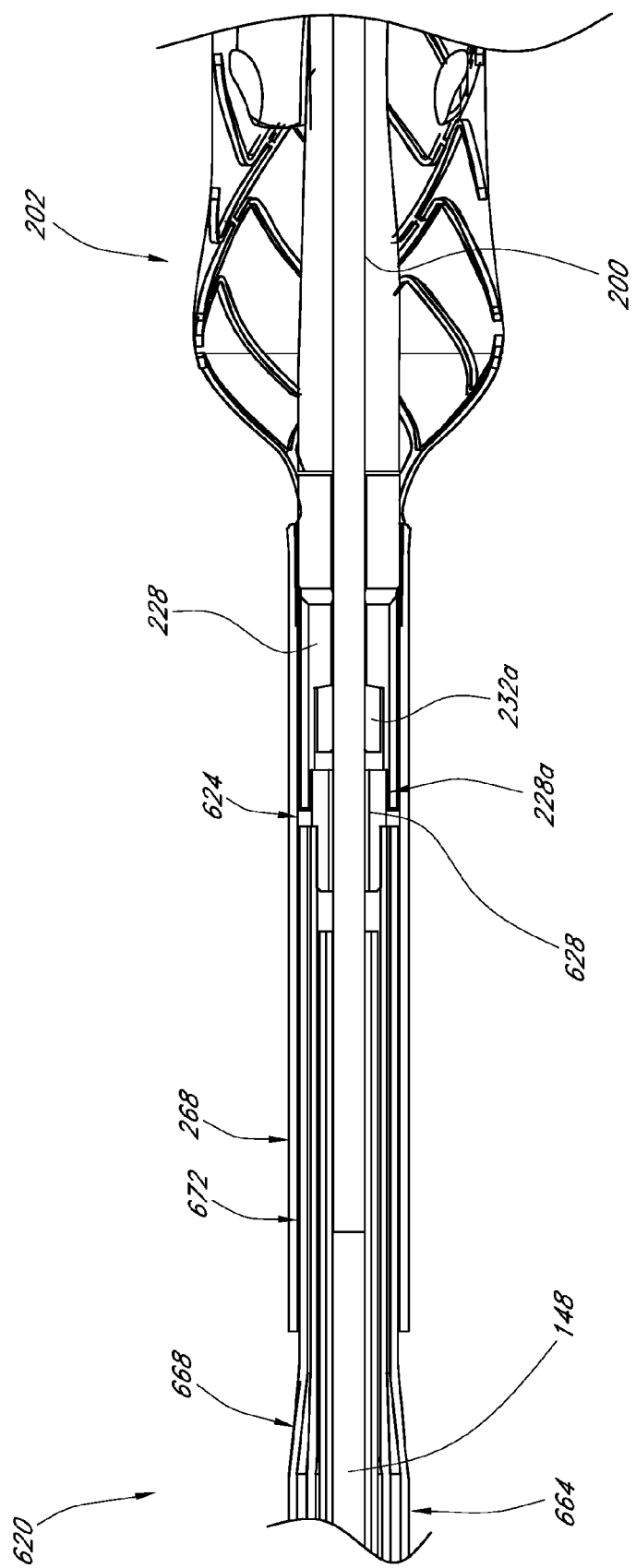
FIGS. 16-18 illustrate another embodiment of a catheter assembly having a simplified construction.
Figure 18:
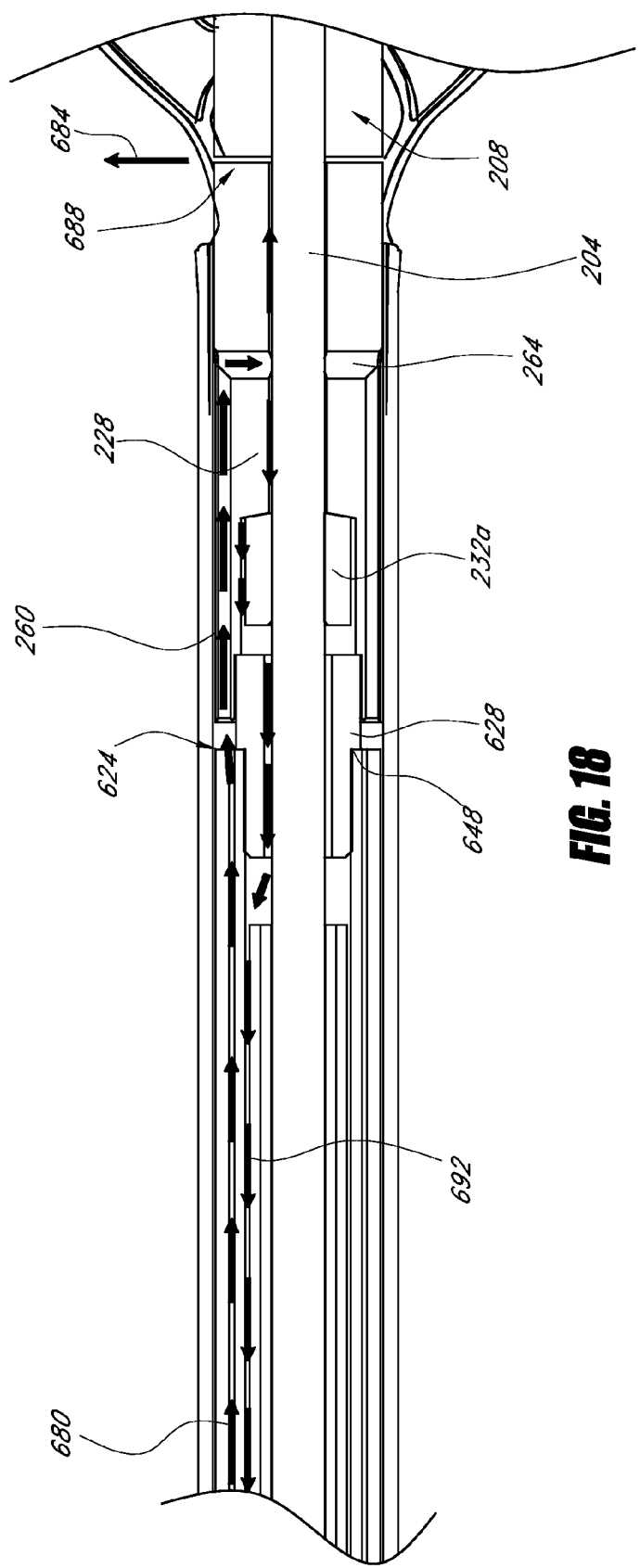

FIGS. 3 to 8 show various structures for providing rotational support of a proximal portion of the shaft 204 within the distal portion of the catheter assembly 100. For example, as shown in FIG. 3, a bearing assembly 220 can be disposed at a distal end 224 of the multilumen catheter body 120. In one embodiment, the bearing assembly 224 includes a housing 228 (as shown in FIG. 4B) and one or more bearings configured to support the proximal portion of the shaft 204. The bearing assembly 224, as illustrated in more detail in FIG. 4B, includes a plurality of bearings 232a, 232b disposed within the bearing housing 228. As illustrated in FIGS. 16 and 18 and discussed further herein, the bearing housing 228 can include a single bearing 232a. Various materials that can be used for the bearing are discussed below.

FIG. 6 shows that the bearing housing 228 has a lumen 234 extending therethrough with a proximal enlarged portion 236a and a distal enlarged portion 236b. The housing 228 comprises a shoulder defining a narrow portion 240 of the lumen 234 disposed between the enlarged portions 236a, 236b. The first and second bearings 232a, 232b can be disposed within the enlarged portions 236a, 236b of the bearing housing 228.

In one arrangement, the proximal end of the shaft 204 (e.g., as shown in FIG. 4A) is received in and extends proximally of the second bearing 232b. In some embodiments, as in FIG. 18, there can be one bearing (e.g., only bearing 232a), while in other embodiments both bearings 232a and 232b can be used. In some embodiments, the bearing(s), e.g., bearings 232a and/or 232b, can be friction fit or interference fit onto the impeller shaft 204. Accordingly, the shaft 204 can be supported for rotation by the bearings 232a, 232b as well as in the narrow portion 240 of the housing 228. In embodiments where the bearing(s) 232a, 232b are friction or interference fit onto the shaft, the bearing(s) 232a, 232b can be configured to rotate with the shaft 204 relative to the bearing housing 228. Further, the bearing(s) 232a, 232b can have a relatively large clearance with the bearing housing 228. The clearance between the shaft 204 and the bearing housing 228, at regions that are not coupled with the bearing, can be in the range of about 0.0005 to about 0.001 inch. In certain embodiments, the clearance can be within a larger range, such as at least about 0.0005 inches, about 0.001 inches or up to about 0.005 inches. In embodiments with multiple bearing(s) 232a, 232b, the clearance can be different for the bearings 232a, 232b, such as providing a larger clearance at the proximal bearing 232a.

Figure 5:
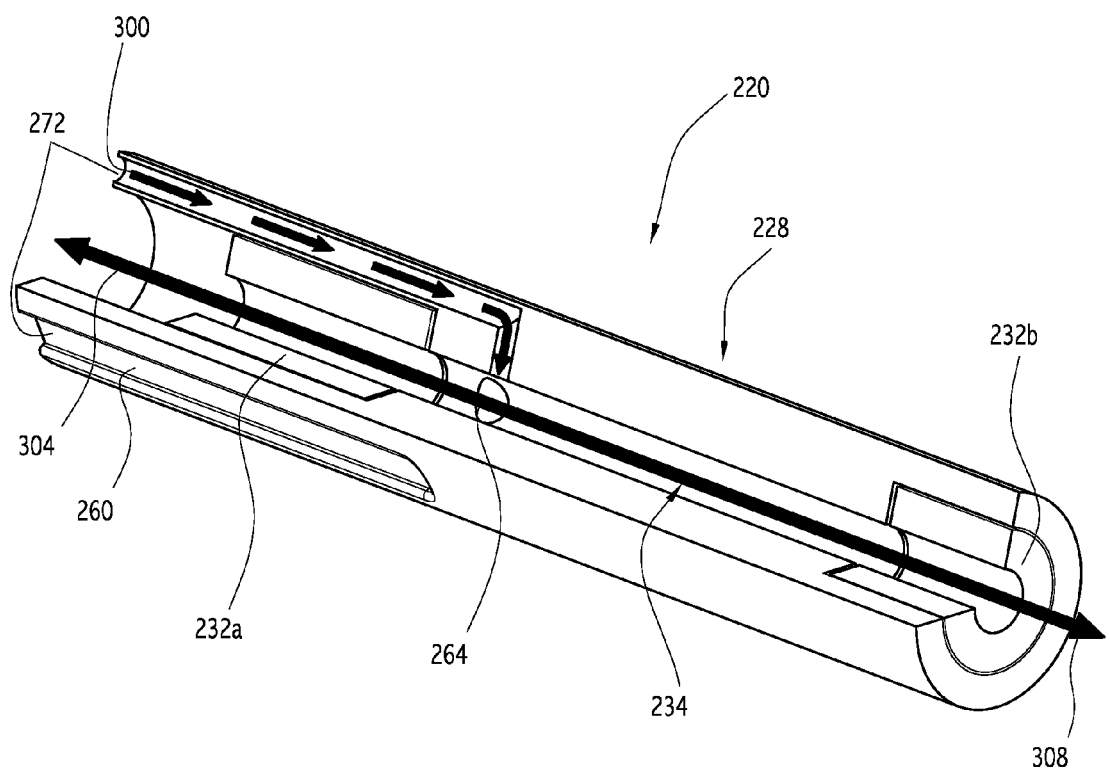
FIG. 5 is a cross-sectional perspective view of a bearing assembly of the catheter assembly of FIG. 1A.

In other embodiments, such as in FIG. 5, the bearing(s) 232a, 232b may not be friction or interference fit onto the shaft 204. In these embodiments, the bearing(s) 232a, 232b may be disposed within the bearing housing 228, for example by an interference or press fit. The shaft 204 may then rotate with respect to the bearing(s) 232a, 232b, and there can be a clearance between the shaft 204 and the bearing(s) 232a, 232b. The clearance between the shaft 204 and the bearings 232a, 232b can be in the range of about 0.0005 to about 0.001 inch. In certain embodiments, the clearance can be within a larger range, such as at least about 0.0005 inches, about 0.001 inches or up to about 0.005 inches. The clearance can be different for the bearings 232a, 232b, such as providing a larger clearance at the proximal bearing 232a. In certain embodiments, the bearing housing 228 may provide a thrust surface for bearing axial loads. In other embodiments, there may be other bearings located either distally or proximally of the bearing housing 228 that are configured to bear axial loads. In other embodiments, the fit between the bearings 232a, 232b and the shaft 204 can be tight, which can also assist in bearing axial loads in some aspects.

At least the proximal portion of the shaft 204 can be made of a material that will not corrode or otherwise be made to be inert when immersed in the lubricant or other infusant. The material may be one that will not corrode in isotonic saline. Suitable materials may include a wide variety of metals, including alloys, and at least saline-resistant stainless steel and nickel-based alloys. Also, the shaft 204 could be made as a composite to include advantageous properties of a plurality of materials. In some cases the shaft 204 could be formed as a polymer. The class of polymers selected would include those that can form a shaft 204 of a certain stiffness suitable in this application. For example, polycarbonate or PEEK could be used. In certain configurations, the polycarbonate, PEEK, or other suitable polymer can provide enhanced performance by being combined with a second material or structure. A glass or carbon filled polycarbonate or other stiff polymer could also be used.

As discussed above, a hydrodynamic bearing between the shaft 204 and the bearings 232a, 232b may be utilized in various embodiments. In one such arrangement, a continuously replenished fluid film is provided at least between the inner wall of the bearing housing and an adjacent moving structure, such as the impeller shaft or an outer surface of a bearing. For example, the bearing housing 228 can be configured to permit a lubricant to be delivered therethrough into the lumen 234. The bearing housing 232 can include a plurality of channels 260 disposed therein extending proximally from a plurality of ports 264 located at the narrow portion 240 of the housing 228. Each port 264 can communicate with one of the channels 260 to provide fluid communication into the lumen 234.

As shown in FIG. 5, the channels 260 can be formed in the wall of the housing 228. In one embodiment, the channels 260 are formed as open depressions, e.g., as flutes, extending along the housing 228. In this embodiment, the channels 260 can be enclosed by a separate structure, such as a separate outer sleeve, that is disposed around the housing 228. FIG. 4B shows that a proximal portion 268 of the impeller housing 202 can be sized to tightly fit over the outer surface of the bearing housing 228, enclosing the radially outward portion of the channels 260. In this arrangement, at least a portion of a flow path is formed between an outer surface of the bearing housing 228 and a separate outer sleeve.

Fluid communication between the port 264 in the bearing housing 228 and the infusion inflow assembly 150 can be by any suitable combination of lumens within the catheter assembly 100. For example, in one embodiment, each of the channels 260 has a proximal port 272 that communications with an annular space 274 formed in the catheter assembly 100. The annular space 274 can be formed between a plurality of separate overlaid structures in the catheter assembly 100. FIGS. 4A and 4B show that the annular space 274 is formed between an outer surface 278 of the multilumen catheter body 120 and an inner surface of the proximal length 268 of the housing 202.

Figure 7C:
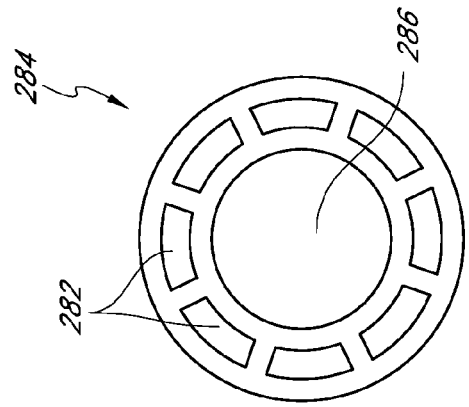
FIGS. 7A-7C show variations of the catheter body of FIG. 7.
Figure 7B:
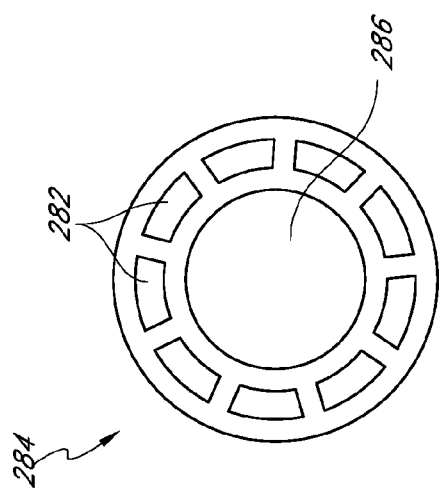
Figure 7A:
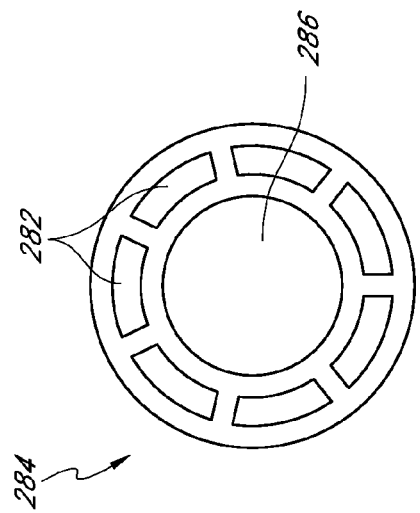

Fluid communication is provided in the catheter assembly 100 between the space 274 and the infusion inflow assembly 150. For example, one or a plurality of lumens 282 formed in the multi-lumen catheter body 120 can be dispersed circumferentially about the catheter body 120 at a peripheral circumferential region 284, as illustrated in FIGS. 7-7C. The peripheral position of the lumens 282 enables a central area of the catheter body 120 to be dedicated to a central lumen 286. By providing a plurality of smaller lumens 282 located at the periphery, a relatively large flow rate can be delivered through a relatively small circumferential band (when considered in cross-section) of the catheter body 120. Each of the lumen 282 has a distal port 290 that communicates with the space 274.

A proximal portion of the lumens 282 can take any suitable form. For example, the lumens 282 can communicate at their proximal end with a flow diverting structure (not shown) that is in fluid communication with the infusion inflow assembly 150. As described herein, in some embodiments the lumen 282 can be disposed circumferentially about the central lumen 286. The catheter assembly 100 can include a flow diverting structure or connector, e.g., disposed about the proximal end of the catheter body 120 that is configured to divert the infusant into the lumens 282 for distally directed flow therein. In other embodiments, the catheter assembly 120 can include a flow diverting structure disposed adjacent the distal end thereof that is configured to divert the infusant into the lumens 282 from the central lumen 286 for proximally directed flow in the lumens 282.

FIG. 5 includes arrows that illustrate the flow of infusant into the bearing assembly 220. In one arrangement, the inflow of infusant is indicated by an arrow 300 which is shown pointing distally within one of the channels 260 of the bearing housing 228. The infusant flow enters the bearing housing through the ports 264. Although flow is shown in one channel 260, corresponding flow may be provided in each of a plurality of channels 260 disposed around the central lumen 234. An arrow 304 illustrates that at least a portion of the infusant delivered through the port 264 flows generally proximally within the bearing housing 228 in various embodiments. An arrow 308 illustrates that at least a portion of the infusant delivered through the port 264 flows generally distally within the bearing housing 228 in some embodiments.

FIG. 5 illustrates the arrows 304, 308 as proximally and distally directed, respectively. However, the high speed rotation of the impeller shaft 204 within the housing 228 will create a thin film of lubricant spacing the impeller shaft 204 from the surfaces of the bearings 232a, 232b. This thin film will extend all the way around the shaft 204 and thus each portion of the flow will have a spiral or helical flow direction.

The bearings 232a, 232b can have different configurations to enhance the performance of the pump 10. For example, the proximal bearing 232a can be longer along the longitudinal axis of the bearing housing 228 than the distal bearing 232b. A longer proximal bearing 232a is believed to better control runout of the shaft 204. Better runout control on the shaft 204 is believed to enhance the control of the position of the blades 212 relative to the housing 202. Less runout reduces excessive variation in the gap between the blades 212 and the housing 202, providing biocompatibility benefits such as reduced hemolysis.

In some embodiments, such as those in FIG. 5 where the bearings 232a, 232b are not friction fit or interference fit onto the shaft 204, the distal bearing 232b has a smaller inner diameter than the proximal bearing 232a. If the shaft 204 has a constant diameter, the smaller inner diameter should provide greater control of angular deflection of the shaft. Controlling angular deflection can enhance relative position control of the blades 212 and housing 202, providing blood handling benefits such as reduced hemolysis. A smaller clearance could also be provided by enlarging the diameter of the shaft 204 at the axial position of the distal bearing. In some embodiments, the larger inner diameter of the bearing 232b enables a larger volume of lubricant to flow proximally and a lesser volume to flow distally in the lumen 234.

The continuous introduction of lubricant maintains a constant, predictable and durable rotational bearing state between stationary component, e.g., the bearing housing 282, and a moving component, e.g., the shaft 204, a component of the bearings 232a, 232b, or both the shaft 204 and a component of the bearings 232a, 232b. Also, continuous lubricant inflow provides a means for removing heat generated by the relative motion between the shaft 204 and the bearings. Also, the infusant can create fluid pressure within the catheter assembly 100 that can push debris generated within or by the pump 10 out of the bearing housing 220. Enhancing the volume of infusant that flows along the path indicated by the arrow 304 enhances the likelihood that debris generated by or present in the pump will be removed from the proximal end rather than to be trapped inside the distal portion of the catheter assembly 100.

Another technique for controlling infusant flow in the lumen 234 is to locate the port 264 between the bearings 232a, 232b and closer to one of the bearing. For example, the ports 264 can be located adjacent to the proximal bearing 232a in one embodiment. This provides a shorter path of egress out of the narrow portion 240 of the bearing housing 228 in the proximal direction.

Figure 8:
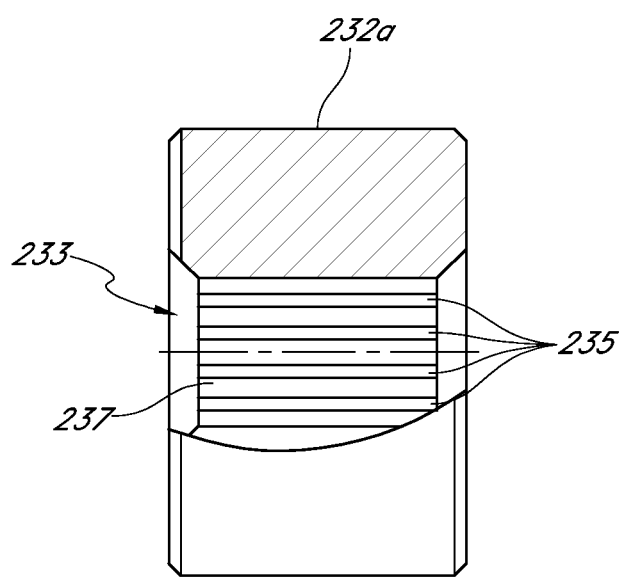
FIG. 8 illustrates a surface configuration of one embodiment of a bearing adapted to enhance or control flow of an infusant in the bearing assembly of FIG. 5.

Other strategies for controlling the flow of infusant within the bearing housing 228 include modifying a surface within one or more of the bearings 232a, 232b. FIG. 8 shows a surface modification 233 provided in a bearing 232a to enhance proximally directed flow. The surface modification 233 comprises a plurality of axially oriented grooves 235 in one embodiment. In another embodiment, the surface modification 233 includes one or more spiral grooves. The spiral grooves can be formed with a groove entrance that is substantially parallel with a flow direction of infusant between the bearings 232a, 232b such that a reduction of velocity of the flow is minimized. In one embodiment, each spiral groove includes at least about 3 turns disposed on the inner surface of the bearing between the proximal and distal ends of the bearing. In another embodiment, each spiral groove has adjacent turns that are spaced apart by a minimum pitch of 0.125 inches (3.2 mm). In another embodiment, each spiral groove has an axial density of about 32 turns per inch (about 1.3 turns per mm). The grooves are formed in the surface 237 of the bearing 232a upon which the impeller shaft 204 is supported. The grooves 235 locally enlarge the clearance between the shaft 204 and the surface 237 so that a greater volume of infusant can flow distal-to-proximal across the bearing 232a. The surface modification 233 reduces back-pressure limiting the distal-to-proximal flow across the bearing 232a.

In other embodiments, it may be desirable to enhance distally directed flow. For example, the infusant may be provided with a fluid intended to be delivered to the patient. In such embodiments, the surface modification 233 can be provided on the distal bearing 232b. In certain embodiments, both proximal and distal bearings 232a, 232b are provided with flow enhancing modifications to enhance heat transfer or purging of the bearing assembly 220. In such embodiments, one of the bearings may have a greater degree of flow enhancement provided on the bearing surface.

The arrangement of the bearing assembly 220 can be a factor in selecting an appropriate infusant. Saline is one type of infusant, but other sufficiently biocompatible infusants could be used. Other embodiments are configured such that little or no infusant flows out of the pump into the patient. For such embodiments, other infusant fluids can be used, such as glucose.

FIG. 7 illustrates further features of the catheter body 120. The catheter body 120 comprises an inner most portion 320 that defines the central lumen 286. The inner most portion 320 is disposed within, e.g., circumferentially surrounded by, the peripheral circumferential region 284. A continuous outer circumferential region 324 can be provided around the peripheral circumferential region 284 to fully enclose the lumen(s) 282, discussed above.

FIGS. 4A and 4B illustrate that a distal end of the inner most portion 320 is configured to be received and secured within a proximal portion of the lumen 234 within the bearing housing 228. FIG. 4B illustrates that a region of overlap can be provided between a distal portion of the inner most portion 320 and a proximal portion of the bearing housing 228. This construction provides a continuous lumen defined in part by the central lumen 286 of the catheter body 120 and in part by the lumen 234 of the bearing housing. Another arrangement is discussed below in connection with FIG. 16-18 in which the bearing housing 228 and the catheter body 120 are joined by a coupler that enhances the sealing between infusant inflow through the lumens 282 and the channels 260 and the infusant outflow through the central lumen 286. As discussed further below, this continuous lumen, also referred to as a drive lumen, can be configured to receive at least a portion of the drive shaft 148 and/or the shaft 204 and provides a space for the rotation of the shaft 204 of the impeller assembly 116 and the drive shaft 148 of the torque coupling system.

The physical connection between the bearing housing 228 and the catheter body 120 can be achieved in any suitable manner. FIG. 3 illustrates that in one arrangement, a slideable connection is provided. In this arrangement, a rod 332 is provided between the bearing housing 228 and the catheter body 120. The rod 332 can have any suitable configuration, but in some embodiments, the rod 332 has a proximal end configured to be received in a recess or lumen formed in the catheter body 120 and a distal end 340 configured to couple with the bearing housing 228. FIG. 3 shows that the distal end 340 of the rod 332 can be configured to engage with a feature of the bearing housing 228 so that a limited range of sliding is permitted.

In one embodiment, the bearing housing 228 has an elongate channel 342 configured to receive a middle portion of the rod 332 and an enlarged depression 344 located at the distal end of the channel 342. The depression 344 has a width W that is sufficient to receive a wide distal end of the rod 332. The depression 344 can be configured to have an axial length along the housing 228 that can define a range of motion of the bearing housing 228 relative to the catheter body 120.

In one arrangement, the bearing housing 228 is positioned relative to the catheter body 120 and the rod 332 such that the distal portion of the rod 332 is located at the distal end of the depression 344. Thereafter, the catheter assembly 100 can be manipulated such that the bearing housing 228 moves distally relative to the catheter body 120 and the rod 332 such that the distal portion of the rod 332 is located at the proximal end of the depression 344. In the distal position, the impeller assembly 116 is located more distally than in the proximal position. As discussed further below, this enables a variety of techniques for unfurling the impeller blades 212 within the housing 202.

B. Bearing Configurations

Any suitable bearing can be used in the catheter assembly 100. The provision of an infusant for hydrodynamic support enables a wide range of bearing materials to be used. If saline or other more corrosive infusant is used, the bearing must be carefully configured to not degrade within the expected duty cycle of the pump 10. Some polymeric materials are advantageously not degraded by isotonic saline, and are acceptable materials from this perspective. Under the fluid-dynamic conditions, a hydrodynamic bearing that is supported by a biocompatible infusant such as isotonic saline is used in various embodiments. It is believed that certain polymer bearings in combination with isotonic saline can support such conditions as 35,000-50,000 psi-ft/min for an appropriate duty cycle. Other aspects that can guide the choice of bearing configurations include minimizing thermal expansion, given the heat that could be generated in the heart pump 10, and minimizing moisture absorption. In some embodiments, a substantially non-swellable material (e.g., a material that absorbs little or no water) can be used for the bearing(s). Advantageously, the use of a non-swellable material can prevent distortion of the bearing, e.g., due to continued exposure to an aqueous environment. Examples of non-swellable materials include some high molecular weight polymers (e.g., having a molecular weight greater than 10,000 Daltons).

Any suitable polymeric material may be used for the bearings 232a, 232b. The polymeric material can include a homopolymer, a copolymer, or a mixture of polymers. The polymeric material can include thermoplastic or thermoset polymers. Examples of polymers that can be used for bearings 232a, 232b include, but are not limited to, one or more of a polyketone, a polyether, a polyacetal, a polyamide-imide, a polyacetal, polyether ether ketone (PEEK), polytetrafluoroethylene (PTFE), and polyphenylene sulfide (PPS). In some embodiments, at least one bearing is a PEEK bearing.

The polymeric material can also include (e.g., can be mixed, combined, and/or filled with) one or more additives such as a reinforcer and a lubricant. Specific additives include, but are not limited to, graphite, carbon fiber, glass fiber, and PTFE. Those of ordinary skill in the art may appreciate that the additives may be polymeric or non-polymeric. In some embodiments, the polymeric material used for bearings 232a and/or 232b can include PEEK, carbon fiber, PTFE, and graphite. In other embodiments, the polymeric material can include PPS and glass fiber. In yet other embodiments, the polymeric material can include a polyamide-imide polymer, carbon fiber, and graphite. The polymeric material can include any suitable amount of additive(s). For example, the polymeric material can include a total amount of additive(s) in the range of from about 1 wt % to about 50 wt %, based on the total weight of the polymeric material. In other embodiments, the polymeric material used for bearings 232a, 232b may not include any additives.

The polymeric material chosen for bearings 232a, 232b can have particular characteristics that advantageously affect the performance of the bearings. For example, in order to minimize thermal expansion caused by the heat generated in the heart pump 10, a preferred material would be subject to a minimum of dimensional change, and can have a coefficient of thermal expansion in the range of from about $1.2 \times 10^{-5\circ}$ $F.^{-1}$ to about $25.2 \times 10^{-5\circ}$ $F.^{-1}$. In other embodiments, the polymer used for bearings 232a, 232b has a coefficient of friction in the range of from about 0.15 to about 0.3. In another example, in order to minimize or prevent water absorption, the selected polymeric material can have a water adsorption in the range of from about 0.01% to about 0.4% over a 24 hour period. In yet another example, the polymeric material can be suitable for high pressure and velocity performance, and can have a limiting pressure-velocity (PV) in the range of from about 20,000 psi-ft/min to about 50,000 psi-ft/min.

The polymeric material used for bearings 232a, 232b may be commercially available. Examples of suitable, commercially-available polymeric materials include, but are not limited to, Ketron PEEK-HPV, Turcite A, Turcite X, Turcite TX, Rulon LR, Rulon J, Rulon 641, Rulon AR, Techtron HPV PPS, Ryton PPS, Torlon 4301, and Torlon 4501. In some embodiments, the polymeric material used for bearings 232a, 232b is Ketron PEEK-HPV.

Of course, other bearing configurations and/or materials would be suitable under other conditions, e.g., with less corrosive infusants or if a hydrostatic or non-hydraulic bearing is used.

Another bearing configuration eliminates one of the bearings, for example, the distal bearing 232b, as illustrated in FIGS. 16 and 18. The bearing 232a can be friction fit, interference fit, or press fit onto the shaft 204, such that the bearing 232a is configured to rotate with the shaft 204 relative to the bearing housing 220 (e.g., there can be little or no clearance between the bearing 232a and the shaft 204). Support for the shaft 204 can be provided by the bearing 232a and the bearing housing 220. In some embodiments, there can be a clearance between the shaft 204 and the bearing housing 228 of between about 0.0005 inches and about 0.001 inches. In certain embodiments, the clearance can be within a larger range, such as at least about 0.0005 inches, about 0.001 inches or up to about 0.005 inches. For example, the lumen 234 extending through the housing 228 can be substantially constant distal of the bearing 232a, e.g., sized to have proper clearance to the shaft 204 along that length. In this embodiment, the distal enlarged portion 236b is eliminated. This configuration is simpler to manufacture and may be less costly. In this embodiment, the bearing 232a can be configured as a thrust bearing to bear axial loads. For example, the bearing 232a can advantageously minimize the distal and/or proximal movement of the impeller 200 (e.g., impeller shaft 204), drive assembly 146, drive shaft 148, and/or elongate body 408 relative to the impeller housing 202. Additionally, the bearing 232a can be configured as a fluid journal bearing, wherein the infusant creates a hydrodynamic layer that can transfer heat during operation and reduce friction between the inner surface or wall of the bearing housing 228 and the outer surface of the bearing 232a. In some embodiments, there can be a large clearance between the thrust bearing 232a and the bearing housing 228. The proximal portion of the bearing housing 228 can also advantageously be configured as a fluid journal bearing, wherein the infusant creates a hydrodynamic layer that can transfer heat during operation and reduce friction between the inner surface or wall of the bearing housing 228 and the outer surface of the impeller shaft 204.

C. Torque Coupling Systems

A torque coupling system is provided to rotate the impeller 200 at a high rate to move blood from inside a heart camber to a location within a patient's vasculature in amounts sufficient to sustain the patient or provide treatment to the patient. The torque coupling system couples the impeller 200 with the motor 14, which may be disposed outside the patient. It is expected that the impeller 200 and the drive shaft 148 are to be rotated at 25,000-30,000 revolutions per minute for a period of seven to ten days. To provide reliable performance under these conditions, isotonic saline or other lubricant is provided between the drive shaft 148 and stationary components therearound.

FIGS. 11 and 4B illustrate proximal and distal portions 400, 404 of the drive shaft 148. The proximal portion 400 is coupled with the drive assembly 146 such that rotation of the drive assembly 146 rotates the drive shaft 148. The distal portion 404 of drive shaft 148 is coupled with the impeller shaft 204 such that rotation of the drive shaft 148 causes rotation of the impeller shaft 204. The drive shaft 148 also includes an elongate body 408 that extends between the proximal and distal portions 400, 404. The elongate portion 408 comprises a lumen 412 extending therethrough.

The size of the elongate body 408 may be as small as possible to minimize the cross-sectional profile of the catheter assembly 100. The cross-sectional profile of the catheter assembly 100 corresponds to the crossing profile of the catheter assembly, which limits where the system can be inserted into the vasculature. The lumen 412 is sized to permit a guidewire to be advanced therethrough in some embodiments. The use of a guidewire is optional, but may simplify insertion.

In one embodiment, the elongate body 408 comprises a multi-layer construction. In some embodiments, each layer can include at least one coil wire or a plurality of coil wires all wound in a same orientation. For example, a two-layer, counter-wound wire construction is particularly advantageous. A first layer (e.g., an inner layer) of the elongate body 408 is provided by a coiled wire of nickel-molybdenum-chromium alloy, such as 35NLT or MP35N. In other embodiments, the wire material can be MP35N LT. In one embodiment, the wire has a 0.008 inch diameter and the coil has a 5 filar right-hand wound construction. The outer diameter of the first layer may be about 0.071 inch. A second layer (e.g., an outer layer) of the elongate body 408 can include the same material as the first layer, disposed on the outside of the first layer. The first and second layers can be wound in the same direction, or in opposite directions. For example, in some embodiments the first layer (e.g., an inner layer) can be left-hand wound and the second layer (e.g., an outer layer) can be right-hand wound, or vice versa. In other embodiments, both the first and second layers can be left-hand wound. In yet other embodiments, both the first and second layers can be right-hand wound. The wound coil wire construction can advantageously facilitate proximal and/or distal flow of infusant along the outer layer of the elongate body 408. For example, the outer layer can be constructed such that the infusant travels along the coil and/or in the direction of the winding. Those skilled in the art may appreciate that, depending on the direction of rotation of the elongate body 408, the infusant flow can advantageously be directed either proximally or distally. The second layer may be a 5 filar left-hand wound construction. In one embodiment, each layer is formed using a 0.008 inch diameter wire, in the above-noted coiled configuration. In other embodiments, the elongate body 408 can include three or more coil wire layers, wherein the layers are wound in alternating directions. In some embodiments, the outer diameter of the second layer can be between about 0.072 inch and about 0.074 inch, while in other embodiments the diameter can be much larger or smaller. In some aspects, for example, the outer diameter of the second layer can be about 0.073 inch. The inner diameter of the elongate body 408 can be at least about 0.039 inch in some implementations. In some embodiments, one or more ends of the elongate body 408 can be welded and square cut, for example, with a 0.1 inch maximum weld length on each end. The length of the elongate body 408 can vary, but in some embodiments, the length can be between about 47 inches and 48 inches, for example, about 47.5 inches.

Other materials and other constructions are possible. The elongate body 408 can be made of other non-ferrous metals or other corrosion resistant material or constructions with appropriate modulus. Other materials that could meet the corrosion requirements include stainless steel (e.g., 302, 304, or 316). In certain embodiments, the elongate body 408 can have a structure that enables other materials to be used. For example varying at least one of coil layers, filars, wire diameter, and coil diameter may enable an otherwise less robust material to operate below the fatigue stress of that material.

In another embodiment, a four layer construction is provided. The four layers comprise three wire-wound layers, e.g., similar to the arrangement described above, but included a third wound layer on the outer surface of the second layer. A low friction layer can be disposed on the outside surface of the elongate body 408. One material that could be used as a low-friction layer is PTFE, known commercially as Teflon®. The low-friction layer should be configured to have sufficient wear resistance, such as by selection of the appropriate PTFE material, e.g. polyphenylene sulphone-filled PTFE, and/or by insuring appropriate infusant flow is maintained during the entire duration of use of the device in order to prevent undesirable local elevated temperature of the PTFE material.

The drive shaft 148 operates within the multilumen catheter body 120. Because the drive shaft 148 is rotated at a very high rate when in use within the multilumen catheter body 120, the configuration of the surface forming the central lumen 286 is important. In various embodiments, this inner surface may have high lubricity and high wear resistance. One material that can be used for the inner surface of the catheter body 120 is high density polyethylene (HDPE), which provides sufficient lubricity and wear resistance. In one embodiment, the entire multilumen catheter body 120 is foamed of HDPE. PTFE provides good lubricity and could be used if made sufficiently wear resistant. One way to increase the wear resistance of PTFE is to impregnate it with polyphenylene sulphone ($PPSO_2$), another is to gamma irradiate the material. One way to increase the lubricity of Polyimide materials is to impregnate it with Graphite, another is to impregnate it with Graphite and PTFE.

FIG. 4B shows a clearance 412 between the elongate body 408 of the drive shaft 148 and the inner surface of the multilumen catheter body 120. The clearance 412 may be at least about 0.005 inch. Along a diameter between opposite sides of the inner surface of the central lumen 286 and outer surface of the elongate body 408 includes about 0.010 inch of space or diametric clearance. A larger minimum clearance may be desirable if the crossing profile can be enlarged or if other structures of the catheter assembly 100 can be made thinner or eliminated to allow more room between the elongate body 408 and the central lumen 286.

FIGS. 11 and 12 show further details of the drive assembly 146, which is disposed at the proximal end 104 of the catheter assembly 100. The drive assembly 146 includes a drive housing 450 having a recess or cavity 454 disposed therein. The cavity 454 is configured for mounting a rotor support shaft 458 for rotation therein. The support shaft 458 has a proximal end and a distal end and a plurality of components mounted thereon. The distal end of the support shaft 458 has a recess 462 formed therein to receive a proximal end of the drive shaft 148. The support shaft 458 may also have a lumen 466 disposed therein for slideably receiving a guidewire.

A rotor 470 is mounted on an outer surface of the support shaft 458 between sleeve bearings 474a, 474b, as shown in FIG. 12. The rotor 470 can take any suitable form, but in one embodiment includes an elongate magnet 476 disposed between proximal and distal flywheels 478a, 478b.

The proximal end of the support shaft 458 has a tapered port 480 for receiving the guidewire. The proximal end can be configured for engaging the motor 14 in some embodiments. In other embodiments, a magnetic field is induced by the motor 14 in a manner that creates torque and rotation of the shaft 458.

An infusant outflow path 482 is provided within the drive assembly 146. The outflow path 482 is provided between an outer surface of the support shaft 458 and an inner surface 486 of the distal bearing. The flow path 482 continues from the distal bearing 474b radially outwardly along thrust surface 490b. The flow path continues proximally between the outer surface of the rotor 470 and the inner surface defining the cavity 454. The flow path 482 continues radially inwardly along the thrust surface 490a toward the support shaft 458. The flow path 482 continues proximally between the support shaft 458 and the proximal bearing 474a. Proximal of the bearing 474a, the flow of infusant exits the catheter assembly 100 through an outflow port 144 through which it can be directed to the waste container 46 or discarded. The flow path is shown in more detail in FIGS. 1, 12, 12A, and 12B.

III. Enhancement of Biocompatibility

The heart pump 10 includes various features that enhance the biocompatibility of the pump. For example, the impeller 200 and the housing 202 are carefully configured to interact with the blood in a way that minimizes hemolysis. Also, the blood contacting surfaces and components of the heart pump 10 can be enhanced to minimize adverse effects within the patient.

A. Impeller Configurations

The impeller 200 may be configured to minimize blood hemolysis when in use, while at the same time providing sufficient flow generating performance. FIG. 9 illustrates some configurations in which the work performed by the impeller blades 212, as defined by the flow-pressure performance, is maximized. In FIG. 9, the proximal and distal impeller blades have tips 212a that can have a generally flat configuration. For example, the flat aspect of the distal tips 212a can be disposed at the outermost end thereof. In another embodiment, the tips 212a can have an arcuate shape about the hub 208. More particularly, the arcuate shape can be a helical shape as shown in FIG. 9.

The flat end portion of the tips 212a provides a surface that is generally parallel to the inner wall of the impeller housing 202. In testing, the flat tips 212a have exhibited optimal hydrodynamic performance.

The number of blades 212 on the impeller 200 can vary. For example, the impeller 200 can have one, two, three, four, five, six, or more total blades 212. As illustrated in FIG. 2A, the impeller 200 can have four total blades 212. In another example, the impeller 200 can have two total blades 212. The axial orientation of the blade(s) 212 can vary. In some embodiments, the blades 212 can be arranged axially along the impeller hub 208 in one, two, three, or more rows. As illustrated in FIG. 9A, for example, the impeller 200 can include two blade rows, each row including two blades. A multiple row arrangement may be advantageous in that the maximum amount of time blood components contact the blade is less than is the case with a comparable single row blade configuration. A two row configuration can result in less contact time compared to a single row configuration. In one example, a blade in a single row configuration has an axial length L1. In the two row configuration, the axial distance from the leading edge of the forward blade to the trailing edge of the rearward blade can also be a length L1. A gap between the two blades in the two row configuration can have an axial length of G1. When flowing through the gap, the blood is not in contact with the blades. This short segment or gap of no blood contact with the blades breaks-up the contact time, which provides better handling of delicate structures of the blood. In other embodiments, the impeller 200 can have two blades total, the blades being arranged in a single row (e.g., wherein all of the blades are at generally the same axial position along the impeller hub 208). Advantageously, an impeller 200 with fewer blade rows can be manufactured more easily than an impeller with a larger number of blades and/or a larger number of rows. In addition, an impeller 200 with fewer blade rows can be deployed and/or retrieved more easily than an impeller with additional blade rows. Note that while, in general, FIGS. 9, 9A, 9B-1, and 9B-2 are representative of certain embodiments of blades and impellers, the disclosed blades may have further features not shown to scale. For example, in some embodiments the blades wrap around the shaft such that the leading edge of each blade is off-set by a substantial amount from the trailing edge of the same blade. For example, the leading and trailing edges can be offset by at least about 10 degrees, in some embodiments up to 40 degrees. In other embodiments, the leading and trailing edges are off-set by up to 90 degrees or more. In some embodiments, a first blade had a leading edge at a first circumferential position and a trailing edge at a second circumferential position, and a second blade has a leading edge at a circumferential position between the circumferential position of the leading edge and trailing edge of the first blade.

The circumferential orientation of the blade(s) 212 from one row relative to another can also vary. As illustrated in FIG. 9B-1, the blades in the first blade row (e.g., blade 213a-1) can be circumferentially staggered, offset, or clocked, from the blades in the second blade row (e.g., blade 213a-2). In some embodiments, the blades can be fully clocked (e.g., no circumferential overlap between blades). In other embodiments, the blades can be partially clocked (e.g., some circumferential overlap between blades). In yet other embodiments, the blades in the first blade row (e.g., blade 214a-1) can be aligned with the blades in the second blade row (e.g., blade 214a-2), for example as illustrated in FIG. 9B-2. The clocked blades can have many advantages, such as increased flow rate, reduced friction, and/or increased ease of deployment/retrieval.

FIG. 10 illustrates another embodiment of an impeller blade 212' that includes modified tips 212b. The distal tips 212b are rounded on suction to pressure side of the blade. The rounding of the tips 212b can result from eliminating one or more edges between the suction side surface and the pressure side surface. For example as show in FIG. 9, some embodiments provide a plurality of sharp edges between the leading edge, trailing edge, and end surface of the blades. By eliminating one or more of these sharp edges a rounded profile is provided.

Without being bound to any particular theory, it is believed that this rounding reduces fluid stress and fluid stress gradient (change in pressure and/or in strain rate per unit length of the fluid flow path) on the constituents of the fluid being pumped. The reduction of such stresses and gradient can provide a more biocompatible interaction of the pump 10 with blood when used as a blood pump. For example, red blood cells can be damaged by being subject to high stresses or to high stress gradients. By reducing exposure of red blood cells to these conditions, hemolysis can be reduced. These benefits can be sustained even where the blades 212' are otherwise arranged to provide equivalent flow performance to the blades 212, such as by providing comparable radial width of the blades 212, 212', rotation speeds, and gaps between the tip 212b and the inner surface of the housing 202.

The configuration of the blades 212' provides the further advantage of reducing sensitivity to the gap between the tip 212b and the inner wall of the housing 202. Where sharp edge configurations are provided, variations in the gap between the tip and the housing wall can greatly affect the flow performance of the pump 10. However, by rounding the edges as in the blades 212', the variation of flow performance is much less due to changing tip gap. Because the housing 202 is flexible and the distal portion of the catheter assembly 100 is disposed in a highly dynamic environment during use this arrangement reduces perturbations in the flow characteristics within the housing 202, providing an even more robust design.

A further advantage of the rounded tip design is that the lessened sensitivity to tip gap provides a better configuration for manufacturing. This arrangement permits wider manufacturing tolerances for one or both of the impeller 200 and the impeller housing 202.

FIG. 10A illustrates further variations of the rounded tip design that combine one or more rounded edges with a flat area 212c at or adjacent the tip of the blade 212". Rounded edges extend from one end of the flat area toward the leading edge of the blade 212" and from another end of the flat area 212c toward the trailing edge of the blade 212". In variations of FIG. 10A, the flat area 212C can be combined with a single rounded edge that extends only toward the leading edge or only toward the trailing edge. One advantage of the combination of the flat area 212c with one or more rounded edges is that this combination maximizes hydrodynamic performance that would occur with a "square edged" tip while providing the benefit of a more gradual change in fluid pressure and fluid stresses resulting in better hemolytic performance that would occur with a rounded tip shape.

FIG. 9A illustrates another embodiment of an impeller blade 213a that includes modified tips 213b. The tips 213b are rounded on the leading edge and trailing edge of the blade. By eliminating sharp edges a rounded profile is provided in the axial direction. Rounding in this fashion provides the same general benefits as the "cross-blade" tip rounding in 212b, 212c. Without being bound to any particular theory, it is believed that this rounding reduces fluid stress and fluid stress gradients on the constituents of the fluid being pumped. The reduction of such stresses and gradient can provide a more biocompatible interaction of the pump 10 with blood when used as a blood pump. For example, red blood cells can be damaged by being subject to high stresses or to high stress gradients. By reducing exposure of red blood cells to these conditions, hemolysis can be reduced.

B. Coatings To Enhance Biocompatibility

In some embodiments, the impeller 200 can include an outer coating layer (not shown). In some embodiments, the outer coating layer can include one or more polymers. The one or more polymers can include a homopolymer, a copolymer, and/or a mixture of polymers. The one or more polymers can be linear, branched, or crosslinked. The one or more polymers can be thermoset or thermoplastic. In some embodiments, the one or more polymers are elastomeric. In some embodiments, the outer coating layer can be hydrophilic. Examples of suitable polymers include, but are not limited to, silicones (e.g., a siloxane), silanes (e.g., an alkyltriacetoxysilane), polyurethanes, acrylics, and fluoropolymers. One example is a siloxane polymer that has been substituted with one or more alkyl, alkoxy, and/or poly(alkyl amine) groups. Polymers suitable for the outer coating layer can be commercially available and/or synthesized according to methods known to those skilled in the art. Examples of commercially available polymers include the Dow Corning MDX line of silicone polymers (e.g., MDX4-4159, MDX4-4210). In some embodiments, the outer coating layer can also include a therapeutic agent, e.g., a drug that limits the ability of thrombus to adhere to the impeller 200. One example of a suitable therapeutic agent is heparin. In some embodiments, the impeller 200 can include two or more coating layers.

In some embodiments, a substantial portion of the entire exposed surface of the impeller 200 is coated with an outer coating layer. In other embodiments, only a portion of the exposed surface of the impeller 200 is coated with an outer coating layer. For example, in some embodiments, one or more impeller blades 212, or portions thereof, are coated with an outer coating layer.

In some embodiments, the impeller housing 202 can include an outer coating layer (not shown). Suitable materials for the outer coating layer of the impeller housing 202 include, but are not limited to, those described herein with respect to the outer coating layer of the impeller 200. In some embodiments, the impeller housing 202 can include two or more coating layers.

In some embodiments, a substantial portion of the entire exposed surface of the impeller housing 202 is coated with an outer coating layer. In other embodiments, only a portion of the exposed surface of the impeller housing 202 is coated with an outer coating layer. In embodiments where the impeller housing 202 includes a plurality of openings, for example as shown in FIG. 4A, the outer coating layer can coat the impeller housing 202 but not the openings. In other embodiments, the outer coating layer can coat the impeller housing 202 and one or more openings, resulting in a substantially closed impeller housing 202.

The outer coating layer can be applied to the impeller 200 and/or impeller housing 202 by methods known to those skilled in the art, such as dip, spray, or flow coating. The outer coating layer can impart one or more advantageous properties to the impeller 200 and/or impeller housing 202. For example, in some embodiments, an impeller 200 that includes an outer coating layer can exhibit reduced thrombosis, reduced hemolysis, increased lubricity, and/or reduced friction as compared to an otherwise similar impeller that lacks an outer coating layer. Although not bound by theory, it is believed that application of an outer coating layer to the impeller 200 can reduce surface friction, which can improve hemolysis performance by reducing drag forces between the blood and the impeller blades. It is also believed that the outer coating layer can assist in the process of deployment and/or retraction by reducing the coefficient of friction between the collapsed or partially collapsed sliding components.

IV. Streamlined Catheter Assembly Connections

FIG. 13 shows another embodiment of a catheter assembly 500 that includes an elongate catheter body 524 and a proximal portion 540 of an impeller housing that provides for enhanced securement of the connection therebetween. The elongate body 524 comprises a central lumen 528 in which a drive shaft operates and a plurality of peripheral lumens 532 through which infusant can be delivered, as discussed above. The impeller housing can be similar to the impeller housing 202 and the elongate body 524 can be similar to the catheter body 120 in many respects, which will not be repeated here.

FIG. 13 shows that adjacent the distal end of the catheter assembly, there is a length over which a distal portion of the elongate body 524 and the proximal portion 540 of the impeller housing, also referred to as a hypotube, are joined. The distal portion of the elongate body 524 can have an outer diameter that is smaller than the inner diameter of the proximal portion 540 of the impeller housing, allowing the elongate body 524 to extend within the proximal portion 540 of the impeller housing. An outside surface of the elongate body 524 contacts an inner surface of the proximal portion 540. The proximal portion 540 of the impeller housing can have a generally cylindrical shape, and can generally be non-expandable.

Because the drive shaft 148 rotates at a very high rate within the lumen 528 when in use, the configuration of the surface forming the lumen 528 is important. In some embodiments, this surface has high lubricity and high wear resistance. High density polyethylene (HDPE) can be used to form the lumen 528.

At the length where the elongate body 524 and proximal portion 504 are joined, the bond between the two is very important because if the bond breaks when removing the catheter assembly 500 from the patient's heart, the proximal portion 540 of the impeller housing could be dislodged and left in the patient. The highly lubricious nature of the elongate body 524 can make securement of these components more difficult. The distal portion of the elongate body 520 and the proximal portion 540 can be connected using an adhesive bond such as glue. However, it may be desirable to replace or supplement such a bond with a mechanical structural engagement.

Figure 15:
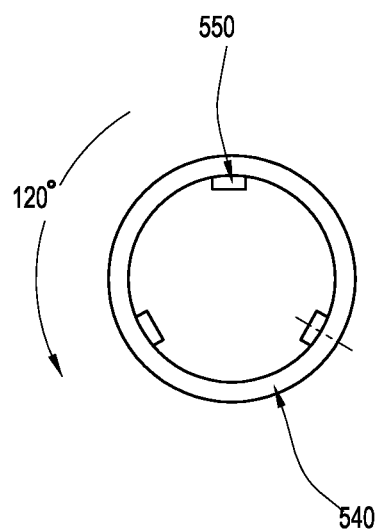

In one embodiment, the adhesive bond can be supplemented by or replaced with a mechanical engagement between the elongate body 524 and proximal portion 540 of the impeller housing. One example of such a mechanical engagement is to use one or more barbs 550. As shown in FIG. 13-15, the barb(s) 550 can be formed at the interface between the proximal portion 540 of the impeller housing 520 and the distal portion of the elongate body 524. The barbs 550 can be formed on the proximal portion 540, for example, such that they are angled inward toward the lumen 528. The shape of the barbs 550 can vary. For example, in some embodiments the barb can be in the shape of a generally rectangular flange. As illustrated in FIGS. 13-14, the proximal portion 540 of the impeller housing can include at least one row of barbs, and in one embodiment, two axial rows of barbs 550. The barbs 550 are much closer to the proximal end of the proximal portion 540 than the distal end thereof. Each axial row can include one or more barbs. In some embodiments, each axial row can include two or three barbs. The barbs can be distributed about the circumference of the hypotube (e.g., the proximal portion 540 of the impeller housing) evenly. For example, on a hypotube having one row with three barbs, the three barbs can be about 120 degrees apart from each other. On a hypotube having two barbs in one row, the two barbs can be about 180 degrees apart from each other.

The angle at which the barbs 550 are formed allows the elongate body 524 to slide or be advanced in one direction (e.g., distally) relative to and into the proximal portion 540, but prevents it from sliding or advancing in an opposite direction (e.g., proximally) relative to the proximal portion 540. Thus, if a tensile force is exerted upon an end of the catheter assembly 500, e.g., when attempting to remove it from a patient, the elongate body 524 will not become separated from the proximal portion 540. More particularly, as the elongate body 524 is pulled in the opposite direction, the barbs 550 in the proximal portion 540 of the impeller housing engage with the outer surface of the elongate body 524. As a force is applied to the elongate body 524 in the opposite direction of insertion, the engagement between the elongate body 524 and proximal portion 504 becomes more secure as the barbs 550 engage with the outer surface of the elongate body 524.

In various embodiments, the barbs 550 are arranged to extend in a direction opposite of a direction of expected application of force. The barbs 550 may comprise cantilevered structures that have a free end disposed away from a connected end. As in FIGS. 13-15, the connected or fixed end can comprise an integral zone of the proximal portion 540 of the impeller housing. The free end extends distally, which is a direction opposite of a direction of force that is expected. As discussed above, a tensile force applied to the proximal end of the catheter body 120, e.g., a tensile force, may be expected upon removal of the catheter assembly 100. In other embodiments, a torsional force may be expected, for example to rotate the catheter body during advancement. For such applications, the barbs 550 can be oriented opposite of the direction of anticipated force. If a clockwise rotation of the catheter body 120 is anticipated, the barbs 550 can extend in a counter-clockwise direction. If a counter-clockwise rotation of the catheter body 120 is anticipated, the barbs 550 can extend in a clockwise direction. The free end can extend generally circumferentially in a direction opposite of the rotational motion of the catheter body 120. The fixed end and free end in the torque transmitting barbs can be at substantially the same axial position.

Although FIG. 13 shows the barbs 550 at an angle to the outer surface of the proximal portion 540, these structures could be parallel to that surface prior to assembly such that the elongate body 524 can be more easily inserted during assembly. Thereafter a tool can be used to bend the barbs 550 inwardly to dig into the outer surface of the elongate body 524.

FIG. 14 illustrates another embodiment in which one or more notches 554 are formed in the outside surface of the elongate body 524. The notches 554 are positioned to correspond to the locations of the barbs 550 of the proximal portion 540. The notches 554 allow a more secure engagement between the elongate body 524 and the proximal portion 540. In addition, the notches provide a tactile confirmation of proper assembly in that the barbs 550 may initially be deformed from a pre-set angled orientation (as shown in FIG. 13) when riding over the distal portion of the elongate body 524. Once the barbs 550 are positioned over the notches 554 they will spring into the pre-set angled orientation.

Advantageously, a distal portion of each barb 550 abuts a proximal edge of each notch 554 such that the proximal portion 540 is prevented from moving distally relative to the notches 554. In particular, the barbs 550 dig into the notches 554 as a tension force is applied in opposite directions on opposite sides of the junction between the elongate body 524 and the impeller housing 502.

FIGS. 13 and 14 illustrate the barbs 550 spaced circumferentially on the proximal portion 540 of the impeller housing by about 180°. In FIG. 15, the barbs 550 are spaced about 120° apart from each other. In further embodiments, the inward angle of the barbs 550, spacing of the barbs 550 circumferentially on the proximal portion 540, number of barbs 550 and notches 512 can all be varied to optimize the engagement between the elongate body 524 and proximal portion B540.

In another embodiment, a plurality of barbs 550 is provided on the proximal portion 540 of the impeller housing where each barb is formed in opposite axial directions to prevent sliding of the lumen 528 in either direction.

In other embodiments, a detent arrangement can be used in place of the barbs 550. Still in other implementations, the barbs could be formed or placed on the distal portion of the elongate body 524 and the notches could be formed on the proximal portion 540 of the impeller housing.

FIGS. 16 and 18 illustrate other embodiment of a catheter assembly 600 that is similar to catheter assembly 100 except as described differently below. In particular, the catheter assembly 600 provides a different manner for connecting a catheter body 620 and the bearing housing 228. In the catheter assembly 600, a distal end 624 of the catheter body 620 is spaced proximally from the proximal end 228a of the bearing housing 228 and a coupler 628 is disposed between the catheter body 620 and the bearing housing 228.

Figure 17:
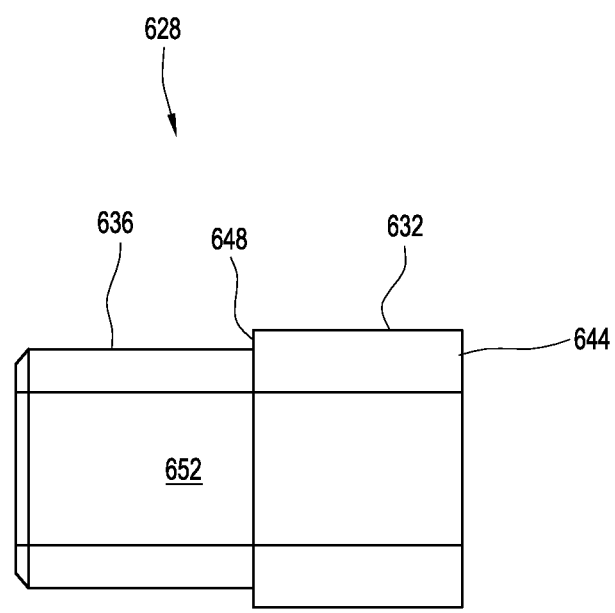

FIG. 17 illustrates one embodiment of the coupler 628, which has a distal end 632 adapted to be inserted into the bearing housing 228 and a proximal end 636 adapted to be inserted into the distal end 624 the catheter body 620. The distal end 632 can have an outer diameter that is approximately equal to an inner diameter at the proximal end of the bearing housing 228. FIG. 6 shows that the bearing housing 228 can include a proximal recess 640 that has an enlarged diameter compared to the diameter of the enlarged portion 236a. FIG. 6 also shows that a shoulder 648 is provided between the recess 640 and the enlarged portion 236a. The shoulder abuts a distal face 644 of the distal end 632 when the coupler 628 is inserted into the recess 640.

The proximal end 636 of the coupler 628 may have a diameter that is less than the diameter of the distal portion 632 such that a shoulder 648 is disposed between the distal and proximal portions 632, 636. When assembled, a distal face of the catheter body 620 is advanced over the proximal portion 636 until the distal face of abuts the shoulder 648.

Advantageously, the coupler 628 can be used to couple the catheter body 620 with the bearing housing 228. A seal and some mechanical securement of the catheter body 622 to the coupler 628 and/or of the coupler 628 to the bearing housing 228 can be provided by disposing an adhesive between these components. For example an adhesive can be disposed between the outer surface of the distal portion 632 and the inner surface of the recess 640 in the bearing housing and between the outer annular surface of the proximal portion 636 and an inner surface of the catheter body 620. The coupler 628 advantageously allows the bearing 232a to be inserted into the bearing housing first in the enlarged portion 236a prior to the securement of the coupler 628 within the recess 640, facilitating convenient assembly. In some embodiments, a seal can be provided in place of an adhesive where securement of the catheter body and the impeller housing in the impeller assembly is provided by other means. For example, the bearing housing can be secured in the proximal portion of the impeller housing by a combination of a tight fit and a strong adhesive. The proximal portion of the impeller housing can be secured to the catheter body by a combination of adhesive and mechanical structures, such as barbs as discussed below in connection with FIGS. 13-15.

One difference between the catheter assembly 600 and certain variations of the catheter assembly 100 is that the coupler 628 fixes the axial position of the bearing housing 228 and the catheter body 620. In the catheter assembly 600, there is no relative axial movement between the catheter body 620 and the bearing housing 228. This arrangement reduces the complexity of the design, providing fewer moving parts, and making it even more reliable. In contrast the catheter assembly 100 permits the bearing housing 228 to slide proximally over the outer surface 278 between distal and proximal positions to facilitate advancement and retraction of the impeller 200 relative to the housing 202. In the proximal position, the annular space 274 is much shorter axially than in the distal position (which is illustrated in FIG. 4B).

The coupler 628 also includes a lumen 652 extending from the proximal end of the proximal portion 636 to the distal face 644. The lumen 652 is adapted to receive a proximal portion of the impeller shaft 204 and to permit infusant to flow between the outer surface of the shaft 204 and the inner surface of the coupler 628 defining the lumen 652.

Returning to FIG. 16, the catheter body 620 has a multilumen configuration similar to that of the catheter body 120, with small peripheral lumens extending proximally and distally and being disposed in a circumferential band around a central lumen. In the catheter body 620, the lumens extend to the distal end of the body 620. In particular, the lumens extend through a proximal portion 664, a tapered portion 668, and a reduced diameter portion 672 of the catheter body 620. In one arrangement, the central lumen 660 has a constant diameter through the portion 664, 668, 672 and the outer surface of the catheter body 620 has varying perimeters (e.g., diameters). The varying perimeter can be pre-formed or induced during assembly of the catheter body 620 to the proximal portion 268 of the housing 202.

FIG. 16 also shows the coupling of the proximal portion 268 of the housing 202 with the catheter body 620. The perimeter of the outer surface of the distal portion 672 may be equal to or less than the inner perimeter or diameter of the proximal portion 268. Accordingly, the distal portion 672 can be inserted into the proximal portion 268 up to the distal end of the tapered portion 668. Securement between the proximal portion 268 and the distal portion 672 can be by any suitable technique, such as adhesive, mechanical interlocking as discussed above in connection with FIGS. 13-15 or a combination of these connections.

FIG. 18 illustrates infusant flow through the catheter assembly 600. Arrow 680 illustrates distal flow of infusant through one of the peripheral lumens, past a portion of the outer surface of the coupler 628 and into the channels 260 of the bearing housing 228. Advantageously, the coupler 628 can assist with directing the distal flow of infusant from the catheter body to the bearing housing 228. As shown, the arrow 680 indicates an infusant flow out of the distal end 624 of the catheter body 620 along an outside surface of the coupler 628 and into the channels 260 that extend distally from the proximal end 228a of the bearing housing 228. As discussed above, the infusant inflow is directed through a plurality of ports 264 onto the impeller shaft 204. Arrow 684 illustrates that a portion of the infusant flows distally between the shaft 204 and a bearing mounted in the bearing housing 228 and out of the catheter assembly 600 through a clearance 688. The clearance 688 can be a space between a distal face of the bearing housing 228 or a bearing disposed therein and a proximal face of a portion of the impeller body or hub 208. Arrow 692 illustrates that a portion of the infusant flows proximally along the shaft 204 in the bearing housing 228. The proximal flow can be directed between the bearing 232a and the bearing housing 228 and thereafter between the coupler 628 and the shaft 204. Thus, the coupler 628 can advantageously direct the infusant proximally from the bearing 232a to the shaft 204 along an inner surface of the coupler 628. The proximally directed infusant then flows into a small annular space between the drive shaft 148 and an inner surface of the catheter body 620 defining the central lumen of the catheter body 620.

In addition to providing a secure connection, the coupler 628, and/or the housing 228 enhances the isolation of distally flowing infusant from proximally flowing infusant. In particular, in addition to having adhesive disposed in the interface between the outside surface of the coupler 628 and the inner surfaces of at least one of the bearing housing 228 and the catheter body 620, the coupler 628 is elongated such that for flow along the path illustrated by arrow 680 to short-circuit into the proximally directed flow 692, the infusant would have to penetrate the length of the coupler 628 defined between the proximal end of the coupler and the shoulder 648. Similarly for proximal flowing infusant along the arrow 692 to be mixed with the distal flow of arrow 680, infusant would have to traverse a substantial potion of (at least a majority of) the length of the coupler between the distal end of the coupler and the shoulder 648.

Thus, the coupler 628 greatly simplifies constructing the catheter assembly 600 and improve the isolation of the inflow and outflow channels for the infusant.

V. Methods

Various methods and techniques are discussed above in connection with specific structures of heart pumps. The following elaborates on some aspects of these techniques and methods. The following discussion is to be read in light of and freely combined with the foregoing discussion.

Deployment, Removal, and Positioning Force Transfer

As discussed above, in various embodiments the heart pump 10 is inserted in a less invasive manner, e.g., using techniques that can be employed in a catheter lab. Various general techniques pertinent to the heart pump 10 are described in U.S. patent application Ser. No. 12/829,359, filed on Jul. 1, 2010, and entitled Blood Pump With Expandable Cannula, which is incorporated by reference herein in its entirety and for all purposes.

Because the catheter assembly 100 is to be delivered through a small access site (e.g., about 11 French or less) and delivered to a remote site in the patient, the method of delivering, removing, and positioning the catheter assembly may be critical. For example, the very secure connection between the catheter body 524 and the proximal portion 540 of the impeller housing enables the clinician to move (e.g., remove) the impeller housing by acting on the proximal end of the catheter assembly. A force (e.g., pulling) applied to the proximal end of the catheter assembly is transmitted by way of the barbs 550 (or other mechanical interface) at a location adjacent to the distal end of the catheter body 524. Thus a clinician can through this method directly transfer the force to the impeller housing by acting on the catheter assembly at the proximal end remote from the impeller housing. This can minimize the chance of the impeller housing becoming disconnected from the catheter body 524, e.g., upon applying a pulling force to retract the impeller assembly with an expanded cannula housing back within a sheath or in pulling the catheter body in retracting the entire device outside of the body.

In some embodiments, a clinician can deploy and remove the impeller housing through the patient's vascular system by applying a longitudinal force parallel to the axis of the catheter body 524. For example, to remove the catheter body 524 and the impeller housing from the patient's body, in some embodiments the clinician can simply apply a force in the proximal direction of the heart pump, e.g., a tensile force, to urge the impeller housing and pump system out of the patient's body. Because the central lumen 528 can have high lubricity, there may be a tendency for the catheter body 524 to slip and become separated from the proximal portion 540 of the impeller housing upon application of a tensile (e.g., proximally directed) force. The implementation of the coupler, the barbs and notches, and other features are designed to prevent and minimize the probability of the catheter body to separate from the distal impeller assembly.

A mechanical interface, such as the barbs 550, can be angled inwardly, as described above, such that an applied tensile force causes the barbs 550 to engage with the outer surface of the catheter body 524 as shown in FIG. 13. In other embodiments, e.g., as shown in FIG. 14, the distal end of the catheter body 524 can include one or more notches 554 configured to engage the barbs 550 upon application of a tensile force to the proximal end of the catheter body 524. When the clinician applies a tensile force to the proximal end of the catheter body 524 in order to remove the impeller housing (and the remainder of the heart pump system) from the patient's body, the barbs 550 can mechanically engage with the proximal portion 540 of the impeller housing to prevent the impeller housing from becoming separated from the catheter body 524. Thus, the use of a mechanical interface between the catheter body and the impeller housing can be used in methods for deploying and removing the heart pump from the patient's vascular system.

As discussed above, the barbs 550 can also be configured for transmitting a torsional force. This can be useful in rotating the catheter within the patient, such as when the clinician desires to position the impeller housing at a certain angle within the vascular system or heart. To position the impeller housing at a particular rotation angle, the clinician can simply apply a torsional force to the proximal end of the catheter body 524. The applied torsional force can be transmitted along the catheter body 524 and to a mechanical interface such as the barbs 550 shown in FIGS. 13 and 14. As mentioned above with respect to FIGS. 13 and 14, the barbs 550 (or other mechanical interface) can be angularly oriented in a direction opposite that of the expected applied torsional force. For example, if a clinician is expected to rotate the proximal end of the catheter body in a clockwise direction in order to position the impeller housing at a desired angle, the barbs 550 may extend in a counter-clockwise orientation. When the clinician applies the clockwise torsional force to position the impeller housing within the patient's vascular system, the applied torsional force can be transmitted in a clockwise direction along the catheter body 524 and to the barbs 550. If the barbs 550 are oriented in a counter-clockwise direction, then the barbs 550 can effectively engage the outer surface of the catheter body 524 (or the notches 554) to transmit the clockwise torque to the proximal portion 540 of the impeller housing, which in turn transmits the torsional force to rotate the impeller housing by the desired angle. Of course, a skilled artisan would recognize that the barbs could be oriented in a clockwise direction as well or any other suitable orientation to resist an applied torsional and/or tensile load.

It will be apparent to those skilled in the art that various modifications and variations can be made in the present embodiments without departing from the scope or spirit of the advantages of the present application. Thus, it is intended that the present application cover the modifications and variations of these embodiments and their equivalents.

What is claimed is:

1. A catheter assembly for a heart pump, comprising
a flexible catheter body having a proximal end and a distal end and defining a plurality of lumens therethrough, the catheter body being sufficiently flexible to extend from a peripheral access to a patient's heart;
an impeller assembly having an impeller and a housing comprising a hypotube sized to be disposed over a distal portion of the catheter body, the hypotube having at least one barb disposed distally such that the barb engages a portion of the catheter assembly disposed inward of the hypotube when tensile forces are applied to opposite ends of the catheter assembly, to enhance the security of the connection between the catheter body and the impeller assembly under such tensile forces.

2. The catheter assembly of claim 1, wherein the hypotube comprises two axial rows of barbs, each row comprising at least two barbs.

3. The catheter assembly of claim 2, wherein the at least two barbs are generally evenly distributed radially about the hypotube.

4. The catheter assembly of claim 1, wherein the at least one barb is in the shape of a rectangular flange.

5. The catheter assembly of claim 1, wherein the hypotube is generally non-expandable.

6. The catheter assembly of claim 1, wherein a proximal portion of the impeller assembly is disposed proximally over a distal length of the catheter body, proximal portion having at least one barb extending circumferentially to engage the catheter body when torsional forces are applied to an end of the catheter assembly.

7. A catheter for a heart pump, comprising
a flexible catheter body having a proximal end and a distal end and defining a plurality of lumens configured to convey an infusant therethrough, the catheter body being sufficiently flexible to extend from a peripheral access to a patient's heart;
an impeller having a shaft and at least one blade;
a bearing housing in which the shaft is journaled for rotation; and
a coupler having a distal end configured to be coupled with the bearing housing and a proximal end configured to be coupled with the catheter body, the proximal end being disposed proximal of the distal end of the lumens of the catheter body;
wherein the catheter assembly is configured such that a first portion of the infusant flows from a distal port in a distal direction over the impeller shaft and a second portion of the infusant flows from the distal port in a proximal direction over the impeller shaft.

8. The catheter of claim 7, wherein the coupler is configured to direct infusant distally from the catheter body to the bearing housing.

9. The catheter of claim 7, wherein the coupler is configured to direct infusant proximally from the bearing housing to the shaft.

10. The catheter of claim 7, wherein the distal end of the coupler is configured to be received within the bearing housing.

11. The catheter of claim 10, wherein the proximal end of the coupler is configured to be received within the catheter body.

12. The catheter of claim 10, wherein the distal end of the coupler has a first diameter and the proximal end of the coupler has a second diameter less than the first diameter.

13. A heart pump configured to be applied percutaneously, comprising:
a catheter assembly comprising a proximal end, a distal end, and an elongate body extending therebetween, the elongate body having a drive lumen extending therethrough;
an impeller assembly comprising an impeller shaft and an impeller disposed on the impeller shaft; and
a drive shaft disposed in the drive lumen, the drive shaft having a plurality of layers;
wherein the drive shaft comprises first and second coil wire layers wound in opposite directions.

14. The heart pump of claim 13, wherein each of the layers comprises a coil wire.

15. The heart pump of claim 13, further comprising at least one bearing coupled with the distal end of the catheter assembly and configured to hydrodynamically support the impeller assembly.

16. The heart pump of claim 13, wherein at least the portion of the elongate body forming the drive lumen comprises a material configured to resist wear and provide enhanced lubricity.

17. The heart pump of claim 13, wherein a gap between the drive shaft and a surface of the elongate body defining the drive lumen is controlled to permit lubricant flow and to minimize distortion of the drive shaft.

18. The heart pump of claim 13, wherein the impeller includes at least one impeller blade having a leading edge surface, a trailing edge surface, a first zone adjacent to the impeller shaft, and a second zone spaced radially away from the first zone, the second zone having a rounded edge spanning from the leading edges surface to the trailing edge surface.

19. The heart pump of claim 13, wherein the impeller includes at least one impeller blade having a rounding feature applied between a suction side surface and a pressure side surface at (1) a leading edge, (2) a trailing edge, and/or (3) tip edge.

20. The heart pump of claim 13, wherein the drive shaft further comprises a guidewire lumen extending therethrough.

21. A heart pump comprising
a catheter assembly comprising a proximal end, a distal end, and an elongate body extending therebetween;
an impeller assembly coupled with the elongate body and comprising an impeller shaft and an impeller disposed on the impeller shaft;
a bearing disposed between the proximal end of the impeller shaft and the distal end of the catheter assembly; and
an infusant inflow port disposed distal of the bearing and configured to direct infusant radially inwardly toward the impeller shaft.

22. The heart pump of claim 21, wherein the heart pump is configured such that when infusant is directed through the infusant inflow port, a first flow rate of infusant is provided proximally along the outer surface of the impeller shaft and a second flow rate of infusant is provided distally along the outer surface of the impeller, the first flow rate being greater than the second flow rate.

23. The heart pump of claim 21, wherein an infusant inflow channel is provided to convey infusant from the proximal end of the elongate body to the inflow port, the inflow channel being disposed at a radial position spaced from a central longitudinal axis of the elongate body, the outer surface of the impeller being disposed between the radial position of the inflow channel and the central longitudinal axis.

24. The heart pump of claim 21, wherein the bearing is a first bearing and further comprising a second bearing disposed distally of the first bearing.

25. The heart pump of claim 24, wherein the first bearing has a length greater than a length of the second bearing.

26. The heart pump of claim 24, wherein a first clearance distance is defined between the first bearing and the impeller shaft and a second clearance distance is defined between the second bearing the impeller shaft, the first clearance distance being greater than the second clearance distance.

27. The heart pump of claim 24, wherein at least one of the first and second bearings includes a material comprising PEEK.

28. The heart pump of claim 27, wherein the material comprises carbon fiber, PTFE, and graphite.

29. The heart pump of claim 27, wherein the material has a coefficient of friction in the range of from about 0.15 to about 0.3.

30. The heart pump of claim 21, further comprising a bearing housing in which the bearing is mounted, the infusant inflow port being formed in an inner wall of the bearing housing.

31. The heart pump of claim 30, comprising a plurality of inflow ports formed in the bearing housing and a plurality of channels corresponding to each inflow port, the channels being disposed at least in part within a peripheral wall of the bearing housing.

32. The heart pump of claim 31, wherein the channels are in fluid communication with a plurality of flow channels formed in an elongate body disposed proximally of the bearing housing.

33. The heart pump of claim 21, wherein the elongate body comprises a multilumen catheter having a central lumen disposed therein and a peripheral lumen disposed radially outwardly of the central lumen, the peripheral lumen being in fluid communication with the infusant inflow port.

34. The heart pump of claim 21, the heart pump is configured such that infusant directed through the inflow port lubricates the bearing and causes distal flow out of the heart pump keeping blood out of the bearing and impeller assembly.

35. The heart pump of claim 34, wherein the infusant flow causes debris to be moved away from the bearing and the impeller assembly.

36. The heart pump of claim 21, wherein at least the impeller comprises a layer disposed on a surface that is exposed to blood when the heart pump is inserted into the patient and operating, the layer is configured to enhance biocompatibility of the pump.

37. A catheter assembly for a heart pump, comprising:
   a flexible catheter body having a proximal portion and a distal portion and defining one or more lumens therethrough, the catheter body having a central longitudinal axis and being configured to extend from a peripheral access to a patient's heart; and
   an impeller assembly having an impeller and a housing in which the impeller is disposed,
   wherein the distal portion of the catheter body and a proximal portion of the impeller assembly are joined along a length, the distal portion of the catheter body being disposed between an overlying member of the catheter assembly and the central longitudinal axis,
   wherein the distal portion of the catheter body is mechanically engaged with the overlying member by a projection of one of the catheter body and the overlying member into the other of the catheter body and the overlying member.

38. The catheter assembly of claim 37, wherein the overlying member comprises an annular member 39. The catheter assembly of claim 38, wherein the annular member comprises a portion of the impeller housing.

40. The catheter assembly of claim 39, wherein the annular member further comprises one or more barbs configured to secure the proximal portion of the impeller housing with the distal portion of the catheter body.

41. The catheter assembly of claim 39, wherein the distal portion of the catheter body comprises one or more notches positioned to engage the one or more barbs.

42. The catheter assembly of claim 38, further comprising an adhesive disposed on a surface of the distal portion of the catheter body to secure the distal portion of the catheter body to a concentrically mounted structure.

43. The catheter assembly of claim 38, further comprising a seal disposed on a surface of the distal portion of the catheter body to reduce leakage along the surface.

* * * * *

UNITED STATES PATENT AND TRADEMARK OFFICE
CERTIFICATE OF CORRECTION

PATENT NO. : 8,597,170 B2  
APPLICATION NO. : 13/343618  
DATED : December 3, 2013  
INVENTOR(S) : Walters et al.

Page 1 of 1

It is certified that error appears in the above-identified patent and that said Letters Patent is hereby corrected as shown below:

In the Specification

In column 16 at line 19, Change "foamed" to --formed--.

In the Claims

In column 27 at line 46, In Claim 13, change "lavers" to --layers--.

Signed and Sealed this
Second Day of September, 2014

Michelle K. Lee
*Deputy Director of the United States Patent and Trademark Office*